US011317857B2

United States Patent
Kahlert et al.

(10) Patent No.: US 11,317,857 B2
(45) Date of Patent: May 3, 2022

(54) PATIENT MONITORING

(71) Applicant: KONINKLIJKE PHILIPS N.V., Eindhoven (NL)

(72) Inventors: Joachim Kahlert, Aachen (DE); Maarten Petrus Joseph Kuenen, Veldhoven (NL); Calina Ciuhu, Eindhoven (NL); Laurentia Johanna Huijbregts, Eindhoven (NL); Ronaldus Maria Aarts, Geldrop (NL); Rick Bezemer, Amsterdam (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 55 days.

(21) Appl. No.: 16/470,583

(22) PCT Filed: Dec. 20, 2017

(86) PCT No.: PCT/EP2017/083740
§ 371 (c)(1),
(2) Date: Jun. 18, 2019

(87) PCT Pub. No.: WO2018/115082
PCT Pub. Date: Jun. 28, 2018

(65) Prior Publication Data
US 2019/0343456 A1 Nov. 14, 2019

(30) Foreign Application Priority Data
Dec. 20, 2016 (EP) ..................................... 16205200

(51) Int. Cl.
*A61B 5/01* (2006.01)
*A61B 5/00* (2006.01)
(Continued)

(52) U.S. Cl.
CPC .............. *A61B 5/4818* (2013.01); *A61B 5/01* (2013.01); *A61B 5/02055* (2013.01);
(Continued)

(58) Field of Classification Search
CPC ..... A61B 5/4818; A61B 5/01; A61B 5/02055; A61B 5/1116; A61B 5/1118; A61B 5/113;
(Continued)

(56) References Cited

U.S. PATENT DOCUMENTS

| 4,510,941 A | 4/1985 | Dunn |
| 6,258,046 B1 | 7/2001 | Kimball et al. |

(Continued)

FOREIGN PATENT DOCUMENTS

| DE | 4130522 A1 | 3/1993 |
| JP | 2004081806 A | 3/2004 |

(Continued)

OTHER PUBLICATIONS

International Search Report and Written Opinion, International Application No. PCT/EP2017/083740, dated Apr. 11, 2018.
(Continued)

*Primary Examiner* — Ankit D Tejani
*Assistant Examiner* — Joshua Brendon Solomon

(57) ABSTRACT

Presented are concepts for monitoring cardio-respiratory function of a patient. One such concept comprises detecting light or sound from the sublingual vasculature using a sublingual sensor unit adapted to be positioned at a sublingual vasculature of the patient's tongue and to generate a sensor output signal based on the detected light or sound. A processing unit adapted to receive at least one of the sensor unit output signal, wherein the sensor unit and the processing unit are arranged to analyze the venous component in the sensor output signal. An output signal from the sublingual sensor may then be used to provide information on cardio-
(Continued)

respiratory parameters like respiration rate and respiration rate variability, for example.

12 Claims, 9 Drawing Sheets

(51) Int. Cl.
*A61B 5/0205* (2006.01)
*A61B 5/11* (2006.01)
*A61B 5/113* (2006.01)
*A61B 7/00* (2006.01)
*A61B 5/0215* (2006.01)
*A61B 5/08* (2006.01)

(52) U.S. Cl.
CPC ............ *A61B 5/113* (2013.01); *A61B 5/1116* (2013.01); *A61B 5/1118* (2013.01); *A61B 5/4812* (2013.01); *A61B 5/682* (2013.01); *A61B 5/7221* (2013.01); *A61B 7/003* (2013.01); *A61B 5/02154* (2013.01); *A61B 5/0816* (2013.01); *A61B 5/0823* (2013.01); *A61B 5/7282* (2013.01)

(58) Field of Classification Search
CPC ..... A61B 5/4812; A61B 5/682; A61B 5/7221; A61B 5/02154; A61B 5/0816; A61B 5/0823; A61B 5/7282; A61B 7/003
See application file for complete search history.

(56) References Cited

U.S. PATENT DOCUMENTS

| | | | |
|---|---|---|---|
| 7,618,376 B2 | 11/2009 | Kimball | |
| 8,233,954 B2 | 7/2012 | Kling et al. | |
| 8,423,112 B2 | 4/2013 | McKenna et al. | |
| 8,721,555 B2 | 5/2014 | Westbrook et al. | |
| 8,740,806 B2 | 6/2014 | Parfenova et al. | |
| 2004/0127800 A1 | 7/2004 | Kimball et al. | |
| 2005/0065447 A1* | 3/2005 | Lee .................. | A61B 5/082 |
| | | | 600/529 |
| 2008/0066753 A1 | 3/2008 | Martin | |
| 2008/0281173 A1 | 11/2008 | Esenal | |
| 2009/0099621 A1* | 4/2009 | Lin .................. | A61N 1/3601 |
| | | | 607/42 |
| 2010/0152599 A1 | 6/2010 | Duhamel | |
| 2010/0204550 A1* | 8/2010 | Heneghan ........ | A61B 5/411 |
| | | | 600/301 |
| 2012/0125337 A1* | 5/2012 | Asanoi ............. | A61B 5/4812 |
| | | | 128/204.23 |
| 2013/0116512 A1 | 5/2013 | Imran | |
| 2013/0184555 A1 | 7/2013 | Chen et al. | |
| 2014/0094670 A1 | 4/2014 | Melker et al. | |
| 2014/0114165 A1 | 4/2014 | Walker et al. | |
| 2014/0276034 A1 | 9/2014 | Eggers et al. | |
| 2014/0296661 A1 | 10/2014 | Zwartkruis-Pelgrim et al. | |
| 2015/0230759 A1 | 8/2015 | Addison | |
| 2016/0007931 A1 | 1/2016 | Rubin | |
| 2016/0019283 A1* | 1/2016 | Gibson ............. | G16H 40/63 |
| | | | 707/610 |
| 2016/0029898 A1* | 2/2016 | LeBoeuf .......... | A61B 5/7271 |
| | | | 600/301 |
| 2016/0354011 A1 | 12/2016 | Stahl | |
| 2018/0035932 A1* | 2/2018 | Massova ......... | A61B 5/14551 |

FOREIGN PATENT DOCUMENTS

| | | |
|---|---|---|
| WO | 2005030038 A2 | 4/2005 |
| WO | 2015187949 A1 | 12/2015 |

OTHER PUBLICATIONS

Lin, H. et al., "Automatic Sublingual Vein Feature Extraction System", 2014, International Conference on Medical Biometrics.
A. Oksenberg et al., "Are we missing a simple treatment for most adult sleep apnea patients? The avoidance of the supine sleep position", J Sleep Res. Apr. 2014;23(2):204-10.
Migliorini, et al., "Automatic sleep staging based on ballistocardiographic signals recorded through bed sensors", 32nd Annual international Conference of the IEEE EMBS, Buenos Aires, Argentinia, pp. 3273-3276 (2010).
Iber, C. et al., "The AASM Manual for the Scoring of Sleep and Associated events, American Academy of Sleep Medicine", 2007.
Redmond, S. et al., "Sleep staging using cardiorespiratory signals" S.J. Redmond et al., Somnologie 11; 245-256 (2007).

* cited by examiner

PATIENT MONITORING

CROSS-REFERENCE TO PRIOR APPLICATIONS

This application is the U.S. National Phase application under 35 U.S.C. § 371 of International Application Serial No. PCT/EP2017/083740, filed on 20 Dec. 2017, which claims the benefit of European Application No. 16205200.5, filed on 20 Dec. 2016. These applications are hereby incorporated by reference herein.

FIELD OF THE INVENTION

This invention relates to patient monitoring, and more particular to monitoring cardio-respiratory function of a patient.

BACKGROUND OF THE INVENTION

Monitoring of a patient, and in particular monitoring of cardio-respiratory function of a patient, is often relevant for an enhanced diagnostics and therapy planning for the patient. Examples of patients for which monitoring of cardio-respiratory function may be beneficial include those suffering from medical conditions such as chronic obstructive pulmonary disease (COPD), sleep-related problems (sleep disordered breathing (SDB) or insomnia, for example), respiratory disorders, asthma, and the like.

In COPD, asthma and SDB, disordered breathing causes an increased intrathoracic pressure and an increased pressure alteration between the inspiration and expiration cycle. This changed intrathoracic pressure changes the transmural pressure on the heart chambers and the central blood vessels which, in turn, has an impact on the distension of the veins, the atrial filling, the ejection fraction, the stroke volume. Ultimately, it has an impact on the pulmonary circulation and therefore influences the circulation in the left side and right side of the heart.

In respiratory disorders in persons without heart failure, the cardiac system is capable to compensate this additional mechanical cardiac stress of the transmural pressure. While the cardiac system may compensate for this effect by rebalancing the cardiac hemodynamics, a persistent cardiac stress may lead to a structural change of the heart and the development of heart failure and disease exacerbation.

Existing monitoring and diagnostic approaches employ catheters and Doppler Ultrasound which are invasive and not applicable for night-time (e.g. sleep) monitoring. Accordingly, most of the patients at risk form such disorders are not monitored.

Sleep analysis is important for correct diagnosis of patients with sleep-related problems like SDB or insomnia. It is also gaining attention from people without sleep disorders who are just interested in their sleep patterns and/or general health and well-being.

During sleep people usually go through different sleep stages, being REM sleep and non-REM sleep, where non-REM sleep can be divided in 4 stages (e.g. non-REM 1-4). A person might also be awake for certain periods once or more during the night. The typically preferred method for measuring these sleep stages is obtrusive as it requires electroencephalogram (EEG), electromyogram (EMG) and electrooculogram (EOG) data to be obtained using electrodes on the face and the head of the subject/patient.

It is known that the combination of heart rate (HR), heart rate variability (HRV), respiration rate and respiration rate variability can distinguish between REM-sleep, non-REM sleep and awake periods. Currently, measuring respiration rate variability accurately typically requires a respiration belt to be fitted around the torso of the patient or a ventilator mask to be fitted on the face of the patient, thus being fairly obtrusive.

Less obtrusive approaches to sleep monitoring are therefore desirable. Once such known and less obtrusive method makes use of pressure sensors positioned strategically in the bed of a sleeping patient. However, measuring HR, HRV, respiration rate, and respiration rate variability with bed sensors has been shown to be inaccurate.

Apart from sleep staging, other things that occur during sleep may be important in sleep analysis. Examples of such events include snoring, teeth grinding (bruxism), yawning, blood oxygenation and the occurrence of apnea events. With specific regard to apnea events, it may be desirable to determining whether apnea events are caused by obstruction (obstructive sleep apnea, OSA) or by the brain's respiratory control centers (central sleep apnea, CSA), and whether OSA or snoring are posture dependent (e.g. only occurring when the patient is lying on their back; for OSA, this is called "positional obstructive sleep apnea" (POSA)). None of the above-mentioned methods for sleep staging are able to take all those things into account and therefore extra sensors are needed when a combined measurement of those factors and sleep staging is desired.

Thus, there exists a need for unobtrusive monitoring concepts for monitoring cardio-respiratory function of a patient. Such an unobtrusive monitoring concept may be beneficial for enhanced diagnostics and therapy planning in relation to many medical conditions, including COPD, sleep-related problems, respiratory disorders, asthma, and the like.

SUMMARY OF THE INVENTION

The invention aims to at least partly fulfil one of the aforementioned needs. To this end, the invention provides devices, methods, computer program products and systems as defined in the independent claims. The dependent claims provide advantageous embodiments.

Thus, the invention provides an apparatus and a corresponding method for monitoring cardio-respiratory function of a patient. Embodiments of the apparatus may comprise a sublingual sensor unit adapted to be positioned at a sublingual vein or sublingual vasculature of the patient's tongue, to detect light or sound from the sublingual vein/vasculature, and to generate a sensor output signal based on the detected light or sound. The apparatus further comprises a processing unit adapted to receive at least one of the sensor unit output signal, wherein the sensor unit and the processing unit are arranged to analyze the venous component in the sensor output signal.

US2010/0152599 describes an oral appliance compliance monitoring system and method. The oral appliance is suitable for wearing in a patient's oral cavity during sleeping periods and has one or more sensors measuring a variety of conditions such as oxygen saturation levels in the oral cavity mucosa. More in particular the sensor is a pulse oximetry sensor. The data generated by the sensor is continuously transmitted to a local scanner which is in communication with a central computer. The computer interprets the data to determine if the patent is wearing the oral appliance in compliance with a prescribed treatment regimen for breathing-related sleep disorders.

DE4130522 describes a sensor inserted under the tongue tip and comprising a light emitting diode emitting light preferably in the 805 nm wavelength region, and a photodetector, preferably a photo cell. Light is reflected from the tongue while the latter is compressed by a pneumatic or hydraulic cushion linked to a pump. The sensor is configured to measure a patient's blood pressure by detecting the volume pulsation in the tongue's arteries. The photodetector is arranged to detect multiple arteries to reduce disturbing influences caused by reactions of individual veins.

Proposed embodiments according to the present invention are based on using the sublingual vein and/or sublingual vein proximity vasculature of a patient's tongue to look at the venous blood volume/flow and that the variations in blood volume/flow in the sublingual vein or vasculature will give information on cardio-respiratory interactions. In this regard, it should be noted that probing only the sublingual vein might not be possible (because the positioning comes very critical) and it might not be desirable either. When an area is probed that is only a very short distance from the sublingual vein, the venules still give the desired signal representative for the respiratory- and blood accumulation-related information. In a preferred embodiment, information is obtained from the arterioles in that area, from which the heart rate, heart rate variability and arterial blood oxygenation can be obtained. For those reasons, in this patent, when reference is made to 'positioned at a sublingual vein', 'aimed at the sublingual vein', or 'sublingual vasculature', it should be understood to include being at an area which is a close distance from (i.e. proximate to) the sublingual vein wherein information from the venules that drain in the sublingual vein can be derived from the signal. This is preferably at a distance less than 1 cm from the sublingual vein, and more preferably at a distance less than 5 mm from the sublingual vein.

Accordingly, in a preferred embodiment a sublingual sensor unit is adapted to be positioned at, aimed at, or proximate the sublingual vein or sublingual venous vasculature of the patient's tongue, preferably at a distance less than 1 cm from the sublingual vein, and more preferably at a distance less than 3 mm from the sublingual vein. When an area is probed that is only a very short distance from the sublingual vein, the venules still give the desired signal representative for the respiratory- and blood accumulation-related information.

The advantage of the sublingual vein is that it lies close to the surface and that the sublingual skin is very thin and optically transparent. Also, the bottom side of the tongue is a highly perfused area. Those properties make the bottom side of the tongue well-suited for photoplethysmography (PPG) monitoring for example. Further, compared to many other veins or vasculature in other places in the body, the sublingual vein or vasculature is of special interest because it drains into the internal jugular vein, which then drains into the vena cava; there is therefore a close connection to the central veins and the right side of the heart. Especially in a lying position information for the right side of the heart and the central veins can be seen derived from the sublingual vein.

Accordingly, in a preferred embodiment the sensor unit is adapted to be aimed at the sublingual vasculature/area on the bottom side of a patient's tongue, preferably in an area close to the base of the tongue, i.e. deep under the tongue, far from the tip of the tongue. This may, for example, enable more of the venous component to be seen in the sensor signals. Proposed embodiments may therefore leverage the raw signal of the sensor.

A signal from the sensor that is representative of detected light or sound from the sublingual vein may then be used to provide information on cardio-respiratory parameters like respiration rate (RR), respiration rate variability (RRV), onset of inspiration, onset of expiration, duty cycle of respiration, Cheyne-Stokes respiration, obstructive sleep apnea (OSA), central sleep apnea (CSA), distinction between OSA and CSA, obstructive flow limitation (Hypopnea), mean transmural pressure, mean blood accumulation, the presence of edema, sighing, yawning, coughing, paced breathing, and pursed breathing.

In this way, there may be provided a tool for determining and/or monitoring a value of a cardio-respiratory parameter that can be used by a medical professional, a general practitioner without the support of a trained cardiologist, for example. It may assist in the diagnosis of dynamic changes of the preload and blood accumulation in heart failure patients. Similarly, it may help to diagnose and stratify persons who are at the onset of developing heart failure and pulmonary edema. Embodiments may also be used to verify the success of a cardiac therapy and/or to monitor disease progression or exacerbation.

Also, embodiments may be used for detecting or monitoring sleep apnea in a sleep study. For example, proposed embodiments may be employed to detect obstructive and central apnea and may distinguish between these.

Further, an embodiment may be used to monitor the cardio-respiratory response of a ventilation therapy and to better control the device settings of a pressure support therapy in COPD and OSA patients.

It is also envisaged that, using a proposed embodiment, a physician can phenotype during wakefulness the cardiac response on natural spontaneous breathing assisted by ventilation support devices (CPAP) and on voluntarily performed breathing manoeuvres like paced breathing, sighing, periodic breathing to prove applicability and risk of a ventilation therapy. Such monitoring of the preload and the venous blood pooling enables a better control of a mechanical ventilator to avoid the accumulation of fluids (edema) in the lung which are caused by a volume overloading in the lung. Accordingly, monitoring of the cardio-respiratory interaction by a proposed embodiment may improve an outcome of a mechanical ventilation and may lower the morbidity risk in critical care patients.

By way of example, embodiments may be used by a general physician or (medically) un-trained person without the support of a trained cardiologist. This may alleviate a need for close monitoring by medical professionals. It may also reduce a need for medical intervention or treatment. Embodiments may therefore relieve healthcare requirements/resources.

Embodiments may further comprise a supplementary sensor module adapted to be positioned in the patient's mouth and comprising a sensor arrangement adapted to sense a value of at least one of: movement; pressure; temperature; and sound and to generate a supplementary sensor output signal based on the sensed value(s). In such embodiments, the supplementary sensor may provide additional information about the patient which may, for example, be useful for improving accuracy of determinations or refining previously obtained values.

In an embodiment, the apparatus may further comprise a processing unit adapted to receive at least one of the sensor output signal and the supplementary sensor output signal and to process at least one of the received signals in accordance with one or more data processing algorithms to determine a cardio-respiratory value of the patient.

By way of example, the cardio-respiratory value may comprise a value of at least one of: respiration rate; respiration rate variability; onset of inspiration; onset of expiration; duty cycle of respiration; Cheyne-Stokes respiration; obstructive sleep apnea; central sleep apnea; obstructive flow limitation; transmural pressure; blood accumulation; coughing; paced breathing; and pursed breathing.

Typical sampling frequencies of the sensor signal may be 32, 128 or 256 Hz, but the sampling frequency might also have a different value. The data-processing algorithm may be adapted to identify low-frequency variations in the sensor output signal, to get information indicative for the respiration. For example, a RR may be observed as the dominant frequency in the range between. 0.08 Hz and 0.5 Hz. In PPG, this frequency band and lower frequencies are referred to as 'DC', as they are lower than the changes caused by heart rate. Changes in the depth of respiration can, for example, be interpreted from amplitude variations of the PPG signal at the respiration frequency. Embodiments may monitor modulation in a low frequency sensor signal component which indicate the signal response to the deviations in respiration (caused by additional stress in the heart for example). Nevertheless, higher frequencies variations in the sensor output signal (for example in the range between 0.6 Hz and 4 Hz) may also be used to provide information on average heart rate. In PPG, fluctuation in the signal caused by the pulsations of the heart are called 'AC' fluctuations. Heart rate variability and arrhythmias may be derived from a high-pass-filtered signal with a threshold frequency of e.g. 0.5 or 0.6 Hz. SpO2 (optically measured arterial oxygen saturation) may be derived from both AC and DC components, while RRV may require determination of the duration of each breath.

The processing unit may be adapted to receive at least one of the sensor output signal and the supplementary sensor output signal, to process the received sensor output signal in accordance with a data processing algorithm to determine a cardio-respiratory value of the patient, and to analyse the determined cardio-respiratory value in combination with the received supplementary sensor output signal to determine at least one of: a refined cardio-respiratory value; an indication of accuracy or reliability; a sleep state of the patient; an activity of the patient; and an indication of event occurrence. Embodiments may therefore take account of a context of the patient, such as their current activity or physical attributes for example.

The sensor unit may be used either in reflective or transmissive mode.

In an embodiment, the sensor unit may comprise at least one of: a PPG (photoplethysmography) sensor; a laser speckle sensor; a laser Doppler sensor; an ultrasound sensor; and a camera. It is noted that that PPG sensors exist that, when placed on the finger or ear lobe, may enable the derivation of RR (respiration rate) from the sensor signal. However, for sensors placed at these locations, it is practically impossible to see the RR by eye from the raw PPG signal. Therefore, RR can only be derived with relatively complex algorithms, which generally take into account modulations in frequency, amplitude and DC-level. Even then, the derived RR is not always correct. In contrast, the raw PPG signal of a PPG sensor aimed at the sublingual vein in accordance with proposed embodiment clearly shows RR, onset of inspiration, onset of expiration and depth of inspiration thereby potentially avoiding the need for complex algorithms and/or extensive processing resources.

Typically, the PPG signal or sensor unit signal is viewed as a low frequency component, considered as DC, and the high frequency component, called AC, contains the blood pulsatility. Accordingly, in preferred embodiments the AC component is used to estimate heart rate, heart rate variability, and/or oxygen saturation, while the low frequency component is used to extract the features related to respiration and venous pooling. Typically, the AC component is detected in the range between 0.5 Hz and 4 Hz and the DC component is detected in the range between 0.08 and 0.5 Hz. Respiration rate (RR) preferably can be observed as the dominant frequency in the range between e.g. 0.08 and 0.4 Hz, and respiration rate variability (RRV) is based on the changes in the RR over time. Accordingly, changes in the depth of respiration can be interpreted from amplitude variations of the PPG signal at the respiration frequency.

Embodiments may further comprise a light source adapted to illuminate the patient's tongue. The light source may be adapted to emit first light having a wavelength within a first range of wavelengths and to emit second light having a wavelength within a second, different range of wavelengths, or more than one light sources might be used, which each have their own specific wavelength band. By way of example, the first range of wavelength may comprise visible light and the second range of wavelengths may comprise infra-red light. In order to derive SpO2, commonly red and infra-red light are used. Since blood in the veins and venules contains more deoxygenated blood than blood in the arteries and arterioles and since red light is absorbed substantially more by deoxygenated blood than by oxygenated blood (while the absorption in infra-red is similar), red light is especially suitable to derive venous information. In order to have a further distinction between venous and arterial information, the red signal and the infra-red signal could be compared, e.g. the infra-red signal might (preferably after weighing) be subtracted from the red signal.

In some embodiments, an ultrasound transducer or ultrasound transceiver may be employed to transmit and sense ultrasound signals to/from the patient's tongue.

Embodiments may further comprise an output interface adapted to generate an output signal representative of a determined or calculated cardio-respiratory value. For example, a user may be advised of cardio-respiratory value exceeding a predetermined acceptable threshold.

Embodiments may further comprise a user input interface adapted to receive a user input signal representative of at least one of: environmental information; patient information; and a limit value representative of an acceptable upper limit of a cardio-respiratory value. Embodiments may therefore be thought of as providing an interface which enables a user to further specify information or data that may be relevant for the purpose of determining or monitoring a cardio-respiratory value. Such user-specified information may enable unique traits, circumstances and/or conditions specific to the user or the environment to be accounted for when determining or monitoring a cardio-respiratory value.

Thus, there may be provided a tool which enables a user to further specify factors to be included in the determination or monitoring of cardio-respiratory function, e.g. by specifying a value or value range for a user attribute or activity. Embodiments may therefore provide input options, increasing the flexibility and power of risk of cardio-respiratory monitoring.

In some embodiments, the apparatus may further comprise a communication interface adapted to communicate with one or more databases so as to obtain at least one of the information that may be used in determining or monitoring a cardio-respiratory value.

There may be provided a portable computing device comprising apparatus for monitoring a cardio-respiratory function of a patient according to a proposed embodiment.

The system may further comprise a display device for displaying a graphical or non-graphical (e.g. auditory) user interface, wherein the graphical user interface is adapted to communicate information about detected or monitored cardio-respiratory function of a patient to a user.

Embodiments may comprise a client device comprising a data processor device. This may be a standalone device adapted to receive information from one or more remotely positioned information sources (via a communication link for example) and/or even adapted to access information stored in a database for example. In other words, a user (such as a medical professional, technician, researcher, patient etc.) may have an appropriately arranged client device (such as a laptop, tablet computer, mobile phone, PDA, etc.) which provides a system according to an embodiment and thus enables the user to provide data or information for the purpose of monitoring cardio-respiratory function of a patient.

The system may comprise: a server device comprising the at least one processor, where the server device may be configured to transmit generated instructions for determining and/or displaying a cardio-respiratory function of a patient to a client device or communication network. In such a configuration, display instructions are made available by a server. A user may therefore link with the server to work with the system.

The processor may be remotely located from the display device, and a control signal may thus be communicated to the display device via a communication link. Such a communication link can be e.g. the internet and/or a wireless communication link. Other suitable short-range or long-range communication links and/or protocols may be employed. In this way, a user (such as a medical researcher, general practitioner, data analyst, engineer, patient etc.) may have an appropriately arranged device that can receive and process information according to an embodiment for monitoring a cardio-respiratory function of a patient. Embodiments may therefore enable a user to remotely monitor cardio-respiratory function of a patient using a portable computing device, such as a laptop, tablet computer, mobile phone, PDA, etc. Embodiments may also enable data retrieval after a monitored time period.

The system may further comprise: a server device comprising the at least one processor; and a client device comprising a display device. Dedicated data processing means may therefore be employed for the purpose of monitoring a cardio-respiratory function or value of a patient, thus reducing processing requirements or capabilities of other components or devices of the system.

Thus, it will be understood that processing capabilities may therefore be distributed throughout the system in different ways according to predetermined constraints and/or availability of processing resources.

According to another aspect of the invention, there may be provided a mouthpiece (or oral appliance) comprising apparatus for monitoring cardio-respiratory function of a patient according to any preceding claim. For example, embodiments may propose the use of a sensor placed in an oral appliance, wherein the oral appliance on the lower teeth houses the sensor. In this way, the sensor may be stably positioned in the mouth, thereby reducing motion artefact. The oral appliance may, for example, be designed such the tongue can rest directly on the sensor. In some embodiments, the sensor may be adapted to be movable with respect to the oral appliance (e.g. under the control of a mechanical or electro-mechanical arrangement), thereby enabling the positioning of the sensor to be optimised or personalised to a specific-patient for example.

According to yet another aspect of the invention, there may be provided a method for monitoring cardio-respiratory function of a patient, the method comprising: positioning a sublingual sensor unit at sublingual vasculature of the patient's tongue; detecting light or sound from the sublingual vasculature; and generating a sensor output signal based on the detected light or sound.

Embodiments may further comprise the steps of: positioning a supplementary sensor module in the patient's mouth, the sensor module comprising a sensor arrangement adapted to sense a value of at least one of: movement; pressure; temperature; and sound; sensing, with the sensor arrangement, a value of at least one of: movement; pressure; temperature; and sound; and generating a supplementary sensor output signal based on the sensed value(s).

In an embodiment, the method may further comprise: receiving, at a processing unit, at least one of the sensor output signal and the supplementary sensor output signal; and processing at least one of the received signals in accordance with one or more data processing algorithms to determine a cardio-respiratory value of the patient. The cardio-respiratory value may comprise a value of at least one of: respiration rate; respiration rate variability; onset of inspiration; onset of expiration; duty cycle of respiration; Cheyne-Stokes respiration; obstructive sleep apnea; central sleep apnea; obstructive flow limitation; transmural pressure; blood accumulation; coughing; paced breathing; and pursed breathing.

The step of receiving may comprise receiving at least one of the sensor output signal and the supplementary sensor output signal, and the step of processing may comprise processing the received sensor output signal in accordance with a data processing algorithm to determine a cardio-respiratory value of the patient. Further, embodiments may comprise the step of analysing the determined cardio-respiratory value in combination with the received supplementary sensor output signal to determine at least one of: a refined cardio-respiratory value; an indication of accuracy or reliability; a sleep state of the patient; an activity of the patient; and an indication of event occurrence, posture of the patient/head orientation.

By way of example, the step of processing the output signal in accordance with a data processing algorithm may comprise identifying low-frequency variations in the sensor output signal.

Embodiments may further comprise the step of illuminating the patient's tongue with light from a light source. This, may for example comprise: controlling the light source to emit light having a wavelength within a first range of wavelengths and to emit light having a wavelength within a second, different range of wavelengths. Preferably, the first range of wavelength may comprise visible light and the second range of wavelengths may comprise infra-red light. The light source may thus comprise one or more light emitting devices.

Embodiments may provide concepts for monitoring one or more cardio-respiratory functions of a patient. The proposed concepts may comprise positioning a sensor at (e.g. adjacent, proximate, next to, neighbouring, etc.) a sublingual vein of the patient's tongue. Light or sound transmitted through the sublingual vein may be detected by the sensor and the detected light or sound may be used (e.g. processed according to one or more algorithms) to determine a value of a cardio-respiratory functions of the patient. Determining the value of a cardio-respiratory function may comprise taking account of historical information relating to previously determined values of the cardio-respiratory function of the patient. Further, additional sensors may be employed to detect one or more supplementary values of other physical attributes or parameters of the patient. Such supplementary values may be used in combination with the detected light and/or determined value of the cardio-respiratory function to infer or determine other information (such as an indication of accuracy or reliability, a sleep state of the patient, an activity of the patient, or an indication of event occurrence for example) and/or confirm/validate the determined value of the cardio-respiratory function. For this purpose, proposed concepts may employ (or be employed on) at least one processor.

Proposed embodiments may further comprise generating instructions for displaying a GUI on a display device using a processor device, wherein the graphical user interface is adapted to communicate information about detected light or sound from the sublingual vein and/or a determined cardio-respiratory value of the patient to a user. Generating instructions for display of a GUI can mean generating a control signal for use by a display device. Such instructions can be in the form of simple images such as bitmap JPEG or other format. However, such instructions can also be more complex allowing real time build-up of the GUI or parts of the GUI on a regular display device such as for example CRT, LCD, OLED, E-ink or the like.

According to another aspect, there may be provided a computer program product downloadable from a communications network and/or stored on a computer readable medium and/or microprocessor-executable medium wherein the computer program product comprises computer program code instructions, which when executed by at least one processor, implement a method according to a proposed embodiment.

The independent claims define analogous advantages features for method and system claims. The advantages explained for the method herein above and herein below may therefore also apply to the corresponding systems.

BRIEF DESCRIPTION OF THE DRAWINGS

The invention will now be described in detail with reference to the following schematic drawings.

DETAILED DESCRIPTION OF THE EMBODIMENTS

Figure 1:
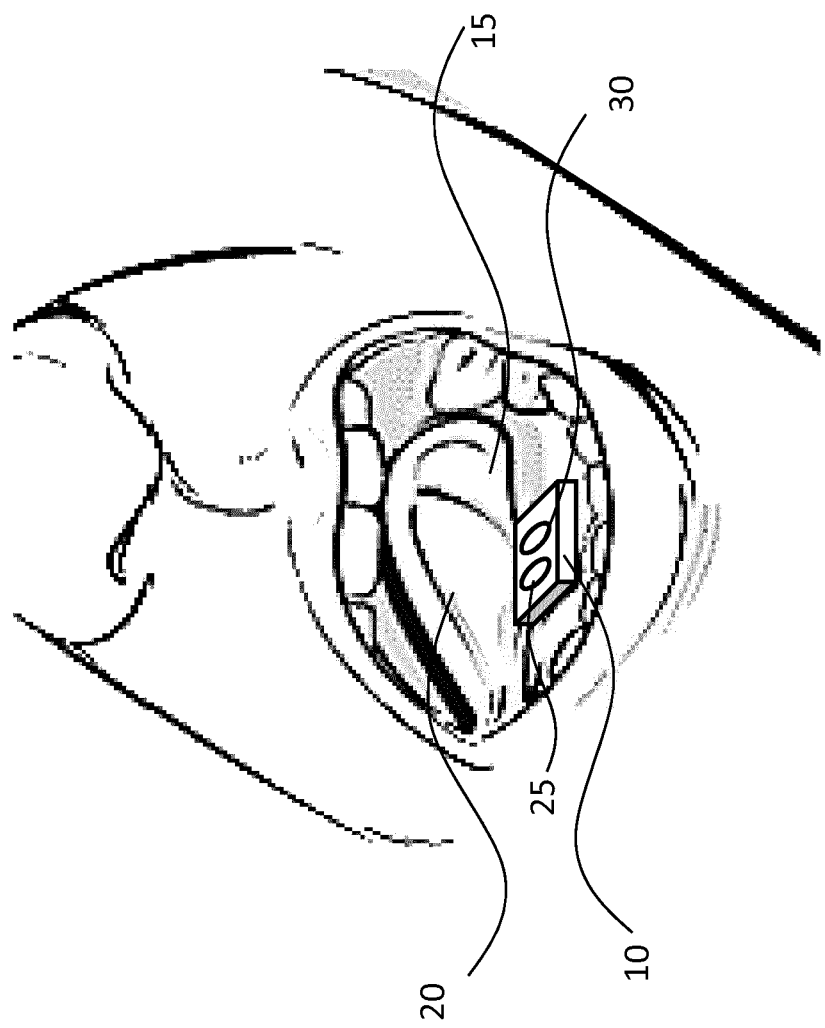
FIG. 1 depicts an embodiment wherein a sublingual optical sensor unit is positioned at a sublingual vein of the patient's tongue.

Proposed embodiments relate to approaches and tools for monitoring cardio-respiratory function of a patient. A sublingual sensor unit may be employed (e.g. positioned) at or near a sublingual vein of the patient's tongue so as to detect light or sound from the sublingual vein or sublingual vasculature. A sensor output signal may then be generated based on the detected light or sound. This signal may be used (e.g. processed) to determine a value of cardio-respiratory parameter of the patient.

Embodiments are therefore based on using the sublingual vein or vasculature of a patient's tongue to detect variations in blood volume/flow in the sublingual veins/vasculature. This approach leverages the fact that the sublingual vein lies close to the sublingual (i.e. bottom or underside) surface of the tongue and that the sublingual skin is thin and optically transparent. Such properties make the sublingual side of the tongue highly-suited for detecting and monitoring blood flow or volume variations.

By way of example, a signal from the sublingual sensor may be used to provide information on cardio-respiratory parameters including: RR, RRV, onset of inspiration, onset of expiration, duty cycle of respiration, Cheyne-Stokes respiration, OSA, CSA, distinction between OSA and CSA, Hypopnea, mean transmural pressure, mean blood accumulation, the presence of edema, sighing, yawning, coughing, paced breathing, and pursed breathing, for example.

Embodiments may therefore be utilized to monitor the cardio-respiratory response of a ventilation therapy and to better control device settings of a pressure support therapy in COPD and OSA patients.

Also, the proposed invention may provide concepts for monitoring one or more cardio-respiratory parameters that can be employed by a general physician or (medically) un-trained person without the support of a trained cardiologist. This may alleviate a need for medical professionals and/or medical intervention, thus potentially relieving healthcare requirements/resources.

Some embodiments may employ a supplementary sensor module, and this may also be adapted to be positioned in the patient's mouth. For example, the supplementary sensor module may comprise a sensor arrangement adapted to sense: movement; pressure; temperature; and/or sound and to generate a supplementary sensor output signal based on the sensed value(s). For example, information regarding sensed motion may be useful for indicating signal quality and/or reliability. Embodiments of the invention may therefore be utilized in conjunction with many different types of additional sensors and/or information databases that may provide contextual information useful for determining a patient's cardio-respiratory function and which more accurately accounts for the specific attributes of the patient, activity of the patient, and/or surrounding environment. A database may comprise, for instance, data relating to the individual's medical history or data relating to cardiorespiratory parameter values in different environmental conditions. For example, information or data employed by embodiments may comprise patient activity, vital signs, temperature, etc.

Embodiments may therefore provide a method, device and/or system that provides for user-specific assessment and monitoring of cardio-respiratory function(s) which takes account of contextual factors (including a physical attributes and activity of a patient, for example) in order to provide more accurate assessment and tracking of cardio-respiratory function or parameter. This may enable measurement and tracking of cardio-respiratory for a specific user, whilst enabling the user to partake in desired activities of daily life. Illustrative embodiments may therefore provide concepts which take account of rules and/or relationships relating to activity and physical attributes of the patient. Dynamic context-based cardio-respiratory function monitoring may therefore be provided by proposed embodiments.

In particular, the present invention is directed toward enabling a user to partake in their normal activities until a time at which a monitored cardio-respiratory function exceeds a predetermined acceptable threshold/limit for example, whereupon the user may be informed of the anomaly and then take appropriate action. This may enable a user to quickly and easily manage activities and exposure to risk. Further, embodiments may communicate information about the cardio-respiratory function in a simple manner (e.g. by visual and/or audible alert) so that a user can readily and easily understand their personal cardio-respiratory function.

As a result, proposed embodiments may be of benefit in any cardio-respiratory function assessment or monitoring applications, especially where users require tailored and/or accurate determination of cardio-respiratory function. One such example may enable patients that are highly susceptible to cardio-respiratory problems to gain a level of independence whilst still managing their potential exposure to cardio-respiratory issues. This may, in turn, improve patient health, hospital efficiency, and available healthcare resources. Embodiments may therefore be of particular benefit for medical applications.

The following description provides a context for the description of elements and functionality of the invention and of how elements of the invention can be implemented.

In the description, the following terms and definitions are used.

A graphical user interface (GUI) is a type of interface that allows users to interact with electronic devices through graphical icons and visual indicators such as secondary notation.

A display device is an electronic display device that can be controlled by a display control device. The display control device can be part of, or operate together with, a processor device.

Generating instructions for displaying a GUI can comprise (or be as simple as) constructing images (Bitmap, JPEG, Tiff or the like) of GUI views to be displayed on a display device using regular methods known in the art. Alternatively, such generation of instructions can comprise more dedicated instructions for real time build-up of a GUI view. The instructions can be in the form of a display control signal.

The invention is at least partly based on the insight that it is advantageous to use a sublingual vein of a patient's tongue for monitoring of blood flow or blood volume so as to determine a value of cardio-respiratory parameter of the patient. In particular, detecting light from the sublingual vein in response to the tongue being illuminated by a light source can be used to accurately determine a cardio-respiratory parameter of the patient. In other words, use of a sublingual optical sensor unit placed at or against a sublingual vein of the patient's tongue so as to detect light from the sublingual vein may be used (e.g. processed) to determine a value of cardio-respiratory parameter of the patient.

Also, detecting sound from the sublingual vein may be used to accurately determine a cardio-respiratory parameter of the patient. For instance, an ultrasound transducer may be employed for converting electrical signals into high-frequency sound waves and vice-versa. In other words, use of a sublingual ultrasound transceiver placed at or against a sublingual vein of the patient's tongue so as to detect reflected sound waves from the sublingual vein may be used (e.g. processed) to determine a value of cardio-respiratory parameter of the patient.

Concepts are thus suggested which propose that the sublingual sensor signal is strongly influenced by the blood volume in the sublingual vein, especially when placed deep (e.g. far from the tip of the tongue or towards the bottom of the tongue, thus close to the tongue connection or base of the tongue). Using such an arrangement, a correlation can be seen with the right side of the heart and the respiratory circuit. Therefore, deriving the respiration rate and respiration rate variability from the signal of the proposed sublingual sensor is easier and more reliable than for usual locations for optical sensors (like the fingertip and wrist, for example).

It will be appreciated that the accuracy of cardio-respiratory parameter determination will depend on the amount and quality of data used.

According to various embodiments, there are proposed several approaches to monitoring cardio-respiratory function of a patient. Turning firstly to FIG. 1, there is depicted an embodiment wherein a sublingual optical sensor unit 10 is positioned at a sublingual vein 15 of the patient's tongue 20.

The optical sensor unit 10 comprises an optical sensor 25 and a light source 30. The light source 30 is adapted to illuminate the underside (e.g. the sublingual vein 15) of patient's tongue 20. More specifically, the light source 30 of this embodiment is adapted to emit light of two differing wavelength ranges, namely a first light having a wavelength within a first range of wavelengths and a second light having a wavelength within a second, different range of wavelengths. Here, the first range of wavelength comprises red light (or light having a wavelength towards the red end of the visible light spectrum) and the second range of wavelengths comprises infra-red light. Of course, in other embodiments, the light source may only emit one type (e.g. wavelength range) of light and/or may emit light of wavelengths different to this example of FIG. 1. For example, green light (e.g. 520 nm) may be employed because it may provide a relatively good signal-to-noise ratio, but light of other colours is also possible.

The optical sensor 25 is a photoplethysmography (PPG) sensor and is adapted to detect light from the sublingual vein in response to the illuminating the patient's tongue with light from the light source 30. Thus, in this example the optical sensor unit 10 may be said to operate in a "reflective mode", because the optical sensor 25 and the light source 30 are both situated under the tongue at the sublingual vein 15. Light from the light source 30 therefore illuminates the sublingual vein 15 of the patient's tongue 20 from underneath the tongue 20 and the light reflected by the sublingual vein 15 is then detected by the optical sensor 25. Other examples may, however, employ an optical sensor unit 10 that is said to operate in a "transmissive mode", wherein the optical sensor 25 situated under the tongue at the sublingual vein 15 and the light source 30 is situated above (e.g. at the upper surface) of the tongue so as to illuminate the tongue from above. In such a transmissive mode, the light source 30 illuminates the patient's tongue 20 from above and the light transmitted through the sublingual vein 15 of the patient's tongue 20 is then detected by the optical sensor 25.

Based on the detected light, the optical sensor 25 generates a sensor output signal for outputting to a signal processing unit.

In this embodiment, the signal processing unit is not integrated into the optical sensor unit 10, but is instead provided as part of a computing device situated near the optical sensor unit (e.g. within a few metres) and outside of the patient's mouth. Of course, in other embodiments, the signal processing unit may be integrated in the optical sensor unit 10.

By way of example only, the signal processing unit of this embodiment is provided as a wearable or clip-on computing device that is worn or carried by the patient. Thus, for communicating the sensor output signal to the signal processing unit, the optical sensor unit 10 comprises a communication interface (not shown) which is adapted to establish a wireless communication link with the signal processing unit. Any suitable short-range or long-range communication links and/or protocols may be employed.

The signal processing unit receives the sensor output signal processes the received signal in accordance with a signal processing algorithms to determine a cardio-respiratory value of the patient. More specifically, the sensor output signal in this embodiment is a raw PPG signal of the PPG sensor 25 and clearly shows RR, thereby potentially avoiding the need for complex algorithms and/or extensive signal processing resources.

The determined cardio-respiratory value of the patient can be communicated to the patient in many different. For example, the patient can be warned if a determined cardio-respiratory value is indicative of a problem or issue (e.g. a cardio-respiratory value is increasing rapidly), and/or determined values for the cardio-respiratory parameter for a predetermined time period (e.g. current day, the past 24 hrs., or a longer period) can be shown to the user, and a warning can be provided if a threshold is reached.

Data obtained for patient can also be shared with other users as a form of community data. However, it is noted that sharing data on identifiable persons as potential infection sources may give rise to privacy issues.

Figure 2:
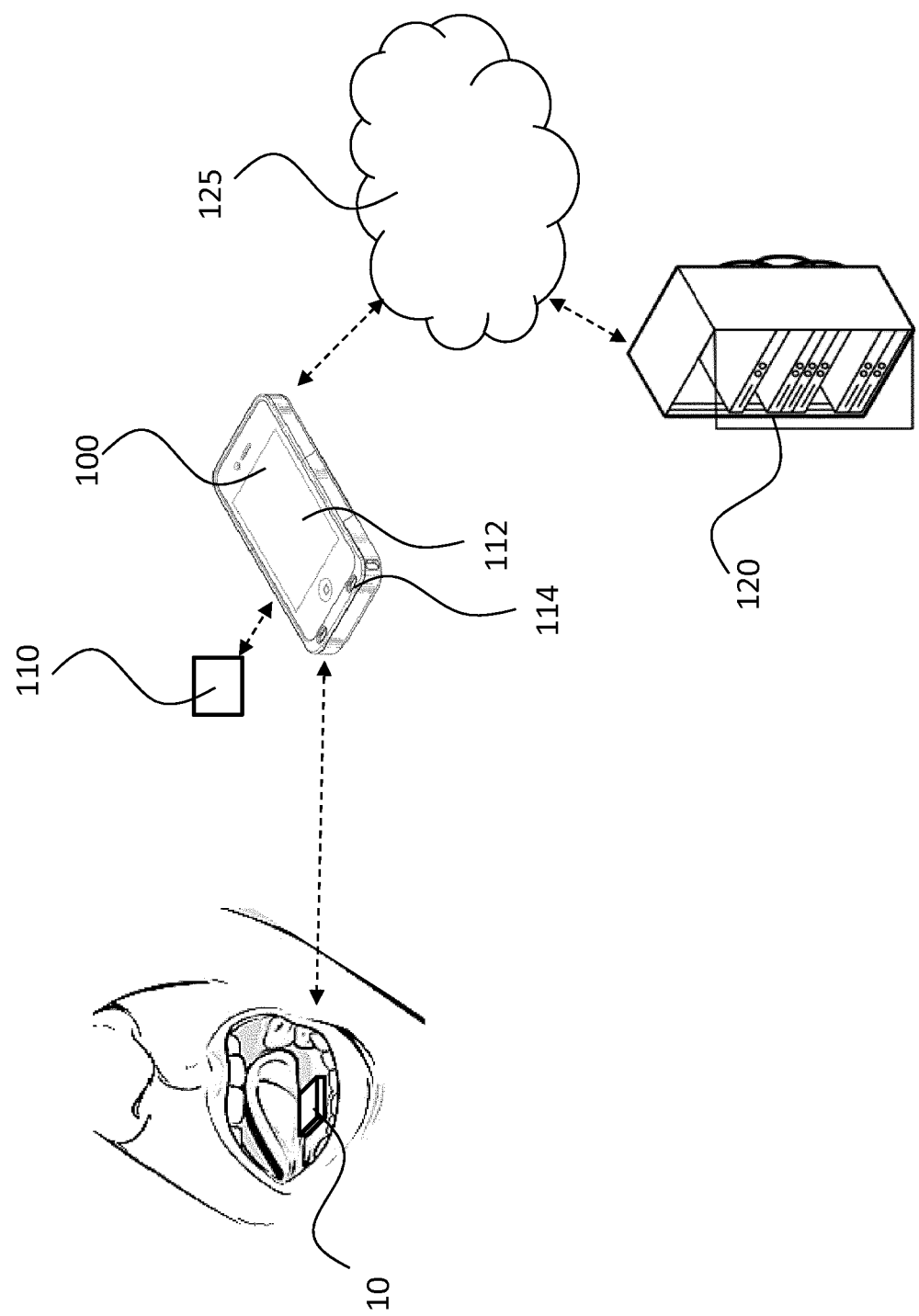
FIG. 2 illustrates an apparatus for monitoring cardio-respiratory function of a patient according to an embodiment.

Turning now to FIG. 2, there is illustrated an apparatus for monitoring cardio-respiratory function of a patient according to an embodiment. In such an embodiment, the apparatus comprises a sublingual optical sensor unit 10 similar to that depicted in FIG. 1 and a processing unit which is integrated in a portable computing device (e.g. a smartphone) 100. Using a built-in communication interface, the portable computing device 100 can receive signals from the sublingual sensor unit 10 and other, supplementary sensors 110, 130 and the process the received signals in accordance with one or more data processing algorithms to determine a cardio-respiratory value of the patient. Further, using the conventional communication abilities of the portable computing device, the device can communicate with one or more databases so as to obtain information that may be used in determining or monitoring a cardio-respiratory value. Such user-specified information may enable unique traits, circumstances and/or conditions specific to the user or the environment to be accounted for when determining or monitoring a cardio-respiratory value.

Also, the display of the portable computing device 100 may be used to display a graphical user interface which communicates information about calculated cardio-respiratory functions to a user of the device.

In more detail, the embodiment of FIG. 2 comprises comprise a client device 100, namely a smartphone 100, comprising data acquisition and processing components. The smartphone 100 is adapted to receive information from sublingual optical sensor unit 10 positioned under a patient's tongue at the sublingual vein via a wireless communication link. Any suitable short-range or long-range communication links and/or protocols may be employed.

The received sensor output signals from the sublingual optical sensor unit 10 thus comprises data that may be used (e.g. processed in accordance with an algorithm so as to determine a value of a cardio-respiratory parameter. For example, the smartphone 100 of this example is adapted to implement a signal processing algorithm which identifies low-frequency optical sensor unit 10 output signal. Here, a RR is observed as the dominant frequency in the range between 0.08 Hz and 0.5 Hz. The smartphone thus implements a software application which monitors modulation in a low frequency optical sensor unit 10 output signal component which is indicative of the signal response to the deviations in respiration (caused by additional stress in the heart for example). Also, higher frequency variations in the optical sensor unit 10 output signal (for example in the range between 0.6 Hz and 4 Hz) are also used to provide information on average heart rate, heart rate variability, arrhythmias and SpO2, for example.

Furthermore, the smartphone 100 is also adapted to receive information from a supplementary sensor unit 110 which is adapted to sense a value of at least one of: movement; pressure; temperature; and sound. The smartphone 100 is adapted to analyse the determined cardio-respiratory value(s) in combination with the received supplementary sensor 110 output signal(s) to determine at least one of: a refined cardio-respiratory value; an indication of accuracy or reliability; a sleep state of the patient; an activity of the patient; and an indication of event occurrence. In this way, a context of the patient (such as their current activity or physical properties for example) can be taken into account in the process of determining and/or monitoring the cardio-respiratory function of the patient.

The smartphone 100 is also adapted to send and/or receive information to/from a remotely located server 120 via the Internet 125.

The information obtained by the smartphone 100 is processed to assess and identify factors which may influence the determined cardio-respiratory functions/parameters of the patient. By way of example, environmental information; patient information; and a limit value representative of an acceptable upper limit of a cardio-respiratory value may be used in the determination or monitoring of a cardio-respiratory value.

The information/data processing may be done by the smartphone 100, by the 'Cloud', or by any combination thereof. The embodiment of FIG. 2 is therefore implemented as a distributed processing environment in which various types of information/data are processed so as to determine or monitor a cardio-respiratory function of the patient.

The smartphone 100 also comprises an output interface, namely a display 112 and speaker 114 arrangement, adapted to generate an output signal representative of the determined cardio-respiratory value/function. For example, if a dangerous cardio-respiratory value is determined or inferred, the user may be advised of the potential threat or danger and guided via voice or visual prompts to mitigate the threat/danger. The smartphone 100 is also adapted to receive (e.g. via its touch sensitive screen 112) a user input signal representative of at least one of: environmental information; patient information; and a limit value representative of an acceptable upper limit of a cardio-respiratory value.

The smartphone 100 therefore provides an interface which enables a user to further specify information or data that may be relevant for the purpose of determining or monitoring a cardio-respiratory value. Such user-specified information enables unique traits, circumstances and/or conditions specific to the user or the environment to be accounted for when determining or monitoring a cardio-respiratory value. Put another way, the smartphone 100 enables a user to further specify factors to be included in the determination of a cardio-respiratory value, e.g. by specifying a value or value range for a user attribute or activity. This provides many input options, increasing the flexibility and power of risk of cardio-respiratory monitoring.

Additionally, or alternatively, further environmental information and/or patient information may be provided by other sources or services. For example, local weather conditions and/or medical history data from a database of the server 120 can be used.

For example, in an exemplary implementation of the system of FIG. 2, the server 120 comprises a data processor unit and is configured to transmit generated instructions for determining and/or displaying a determined cardio-respiratory value to a client device or communication network. In such a configuration, display instructions are made available by the server 120. A user of the smartphone 100 can therefore link with the server 120 to work with the system. In this way, data processing means are remotely located from the portable computing device 100, and a control signal can thus be communicated to the portable computing device 100 via a communication link (e.g. the Internet 125).

Accordingly, a user is provided with an appropriately arranged device that can receive and process information relating to a cardio-respiratory function of a patient. Embodiments may therefore enable a user to monitor a cardio-respiratory parameter over time using a portable computing device, such as a laptop, tablet computer, mobile phone, PDA, etc. The portable computing device 100 therefore provides a tool that enables the user, for instance, to monitor their cardio-respiratory function as they go about their normal activities. The user can obtain an understanding of their cardio-respiratory function, which then enables the user to continue or adapt their planned activities (depending on their tolerance to cardio-respiratory issues for example). Also, a medical professional, technician, researcher, etc. may have an appropriately arranged client device (such as a laptop, tablet computer, mobile phone, PDA, etc.) which is adapted to receive information relating to cardio-respiratory function of a monitored user (e.g. patient). In this way, a user can be provided with guidance at a personal level which takes account of the unique attributes and/or activities of the user, and/or the surrounding environment. This alleviates a need for close monitoring by medical professionals or caregivers, for example. It may also reduce a need for medical intervention or treatment (required as a result of repeated infection for example).

Dedicated data processing means can therefore be implemented at the server 120 for the purpose of determining cardio-respiratory value of a patient, thus relieving or reducing processing requirements at the portable computing device 100.

Thus, it will be understood that processing capabilities may therefore be distributed throughout the system in different ways according to predetermined constraints and/or availability of processing resources of specific embodiments.

Now to aid further understanding of the proposed concepts, an exemplary embodiment that has been implemented in experiments will be described.

In some experiments, the optical sensor comprised a reflective PPG sensor arrangement that contained two green LEDs and a photodiode. In other experiments, however, the optical sensor further comprised two red LEDs. In principle, the number and colour of the LEDs need not be limited, although it is envisaged that certain colour combination may exhibit improved performance. Also the number of photodiodes may be increased beyond one.

The PPG sensor is placed in an oral appliance (or "mouthpiece"). Also, for improved stability, the PPG sensor is placed at an angle (e.g. 45 degrees) with respect to the teeth of the patient. In this way, the device remains fixed in position (because it is supported by the teeth) and the tongue rests on the part that includes the PPG sensor. This minimizes any motion artefacts, while still allowing normal tongue movements such as in swallowing and speech.

To control the pressure and to avoid excessive pressure, smart flexible material can be used. Potentially, an active control of the pressure is possible.

The PPG sensor is attached to the processing unit by a cable. However, as has been explained above, wireless communication between the optical sensor unit and processing unit is envisaged in many embodiments. Indeed, by way of example, data between the sensor unit and the processing unit can be transferred either optically by a fibre, electrically by a cable or wirelessly.

It is also noted that components of the oral appliance may be battery-powered, although it is envisaged that the sensor unit may be charged either by the processing unit or wirelessly by an electromagnetic coupling device in preferable embodiments.

The PPG signals (i.e. the PPG sensor output signals) are transmitted in real-time to the processing unit, where they are analyzed and stored. Alternatively, or additionally, the data can be stored on the oral appliance and/or the processing unit can be integrated into the oral appliance.

Typically, the PPG signal is viewed as a low frequency component, considered as DC, and the high frequency component, called AC, contains the blood pulsatility. Thus, the AC component can be used to estimate heart rate, heart rate variability, and oxygen saturation (in case multiple wavelengths are used) and may therefore be in the range between 0.5 Hz and 4 Hz. The low frequency components, on the other hand, can be used to extract the features related to respiration and venous pooling.

For example, the heart rate (HR) can be observed as a dominant frequency in the range of 0.5 Hz and 3 Hz. For example, respiration rate (RR) can be observed as the dominant frequency in the range between e.g. 0.08 and 0.4 Hz, and respiration rate variability (RRV) is based on the changes in the RR over time. Accordingly, changes in the depth of respiration can be interpreted from amplitude variations of the PPG signal at the respiration frequency.

Figure 3:
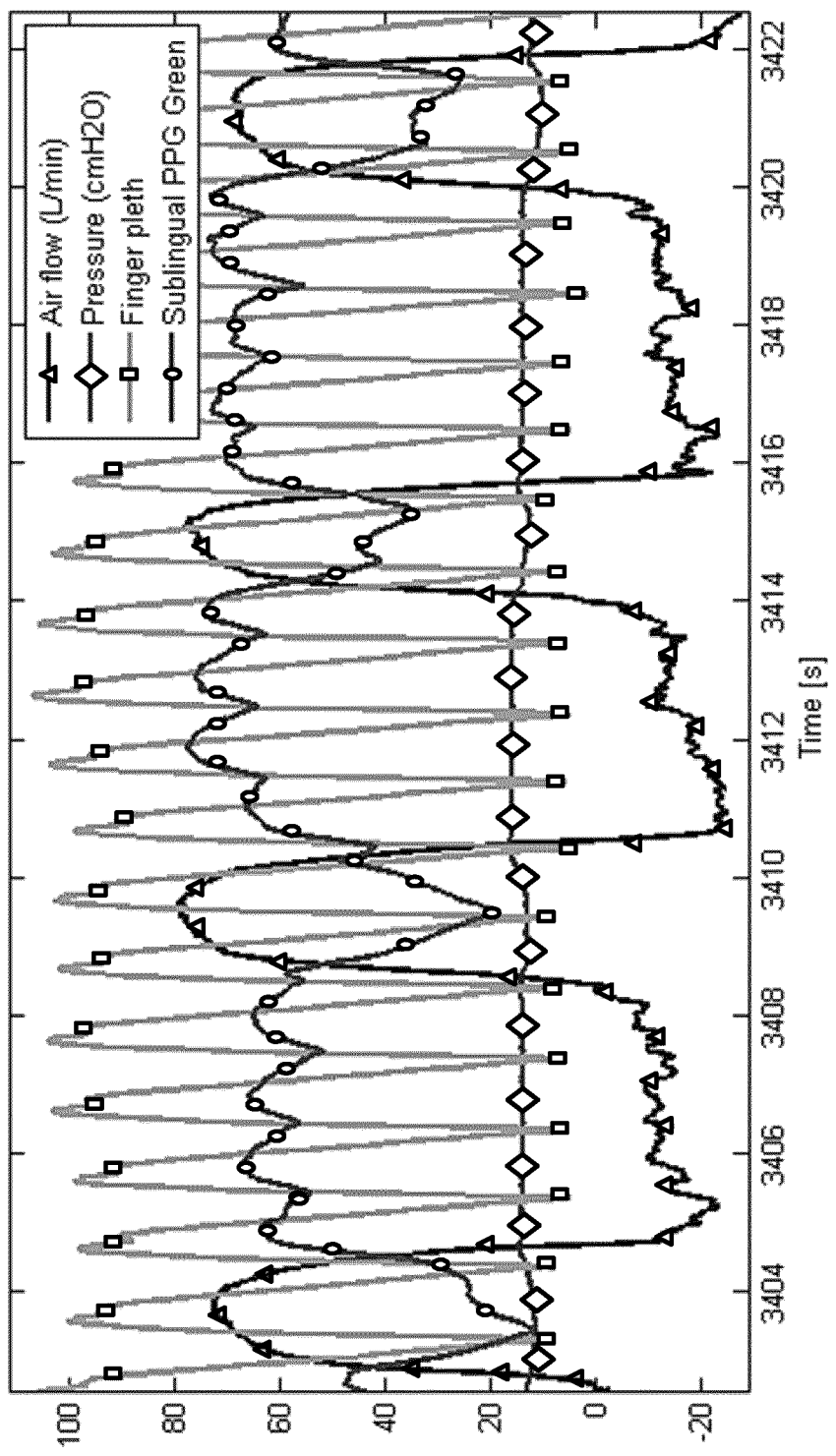
FIGS. 3 and 4 depict the PPG signals and breathing parameters obtained over time by an experimental implementation of an embodiment during spontaneous breathing against a positive airway pressure provided by a mask, wherein FIG. 4 has a longer timescale (on the X-axis) than that of FIG. 3.

Modulation in the lower frequency component of the PPG, indicating the signal response to the deviations in respiration, for example, caused by additional stress in the heart, was simulated in experiments. Nevertheless, in some embodiments, the AC signal component could also be part of the sensor output signal and processed to obtain information regarding average heart rate, heart rate variability, arrhythmias and SpO2. As shown in FIG. 3 the AC signal component of the beating heart (typical range of 0.5 Hz and 3 Hz) and the AC signal component of the respiration cycle (typical range of 0.08 and 0.4 Hz) can be observed in the time domain.

The effect of venous blood pooling can be observed in the acquired PPG signal over time during spontaneous breathing in patients and healthy subjects during sleep and wakefulness. In particular, during voluntary respiration manoeuvres and/or respiration manoeuvers assisted by ventilation support devices, the hemodynamic response of the cardiac system can be studied. These voluntary and assisted respiration manoeuvres create a change and a modulation of the preload on the right side of the heart. A quantified analysis provides a diagnosis of the implication of a respiratory disorder on a healthy heart. Also, for a patient who is treated by a ventilation support device, the impact of the ventilation therapy and its implication on the cardiac system can be studied, and the settings of the ventilation support system can then be optimized to lower the mechanical stress on the cardiac system on the one hand and to provide a sufficient airflow on the other. This will balance the ventilation and the pulmonary circulation in patients suffering from respiratory disorder and a diseased heart.

Figure 4:
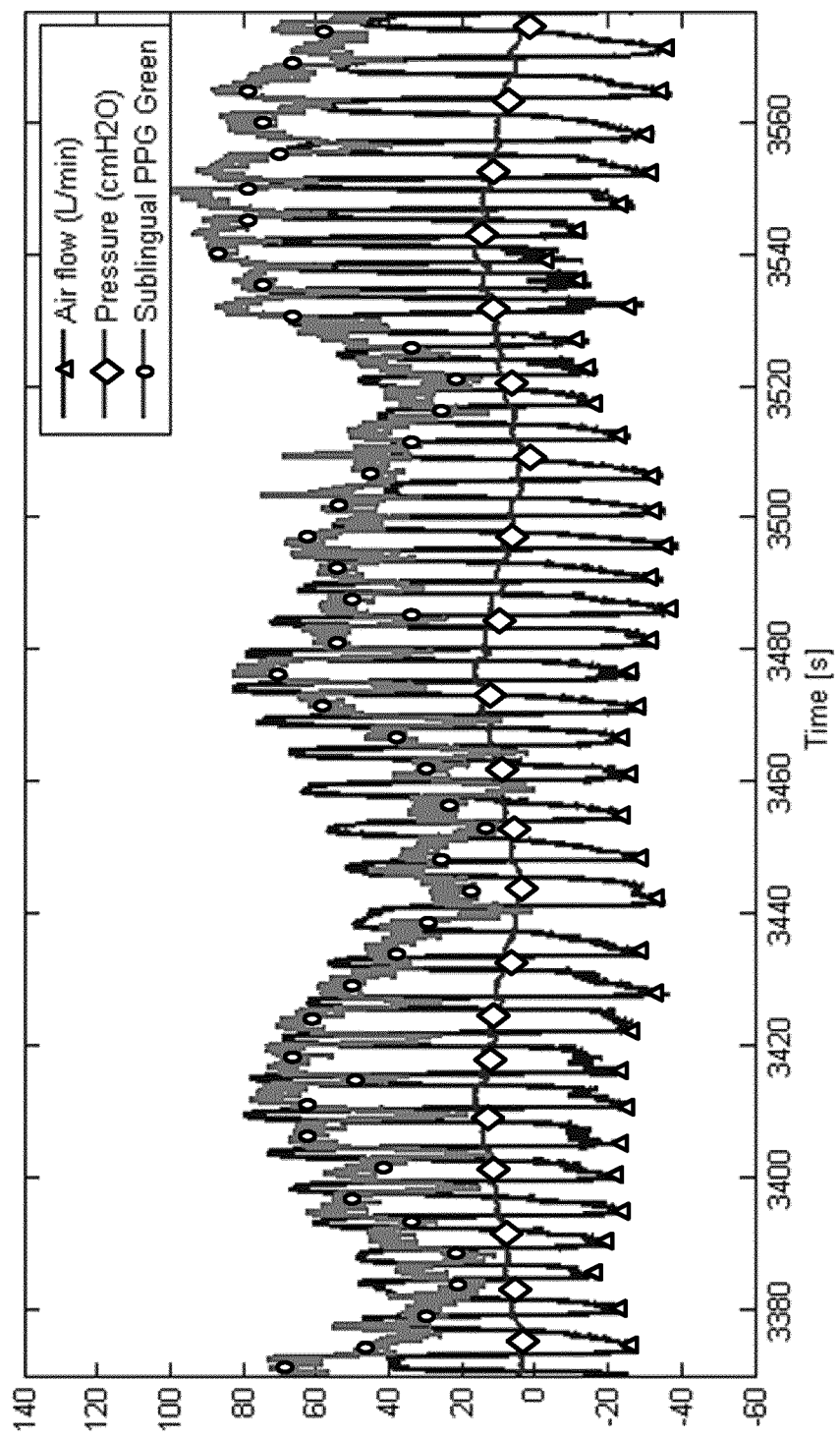

FIGS. 3 and 4 depict obtained signals over time for the experimental implementation, namely signals representing measurements of air flow, airway pressure (provided by a ventilation support device), finger PPG- and sublingual PPG sensor output. More specifically, FIGS. 3 and 4 depicts the PPG signals and breathing parameters observed during spontaneous breathing against a positive airway pressure provided by a mask, wherein FIG. 4 has a longer timescale (on the X-axis) than that of FIG. 3. From FIGS. 3 and 4, it is seen that the PPG signal of the sublingual sensor correlates with respiration (air flow measure by the mask).

In more detail, for the measurements, the intrathoracic pressure was modified by a Continuous positive airway pressure (CPAP) device. The PPG signal observed at the tongue (best visible in FIG. 3) clearly varies in correspondence with the respiratory cycle and the inspiratory and expiratory airflow (which can be seen as the line labelled "Air flow (L/min)").

The high frequency components correspond to the heart rate/pulse frequency. Thus, the sensor enables the monitoring of HR, HRV and arrhythmias.

The low frequency component corresponds to the respiration cycle, which thus enables monitoring of respiration rate, respiration variability and singular breathing pattern. The notches in the sublingual PPG signal, observed in FIG. 3 as a drop in PPG signal amplitude of 20-40 at 3404, 3409, 3415, and 3421 seconds, respectively, enable a quantified analysis of the cardio-respiratory interaction which is specific for the alteration transmural pressure being the indicator for the respiratory induced changes of the cardiac preload of the right-side of the heart. For example, the amplitude of the PPG signal component at the respiration frequency can be used for this analysis. In another example, the time of delay between when inspiration takes place and when the inspiration is seen in the sublingual PPG signal can be used as a measure for the central venous blood pressure. The time of inspiration can be measured by a flow sensor (like in FIG. 3 integrated in a ventilation support device) or with for example a respiration belt around the torso. This time is then subtracted from the time at which the inspiration is seen in the sublingual PPG signal. Note that in FIG. 3 the signals from the ventilator support device and the sublingual sensor were artificially synchronized and do therefore not display the real delay time. In a preferred solution, the two signals are captured in real time with the same clock as reference. Other delay times, like the delay between the sublingual PPG signal and a PPG sensor on another location, are also of interest for measures of blood pressure or blood accumulation.

On the longer time scale of FIG. 4, it is observed that the PPG signal at the tongue (labelled "Sublingual PPG Green") also correlates with the CPAP pressure level (labelled "Pressure (cmH2O)"), showing that the PPG signal is indicative of the intrathoracic pressure.

In COPD patients, the quantified analysis of the notch provides a calculation of the Intrinsic Positive End-Expiratory Pressure (iPEEP). Also, in heart failure patients, the analysis of the notch is characteristic feature for the atrial refilling and the dilatation of the atrium.

Figure 5:
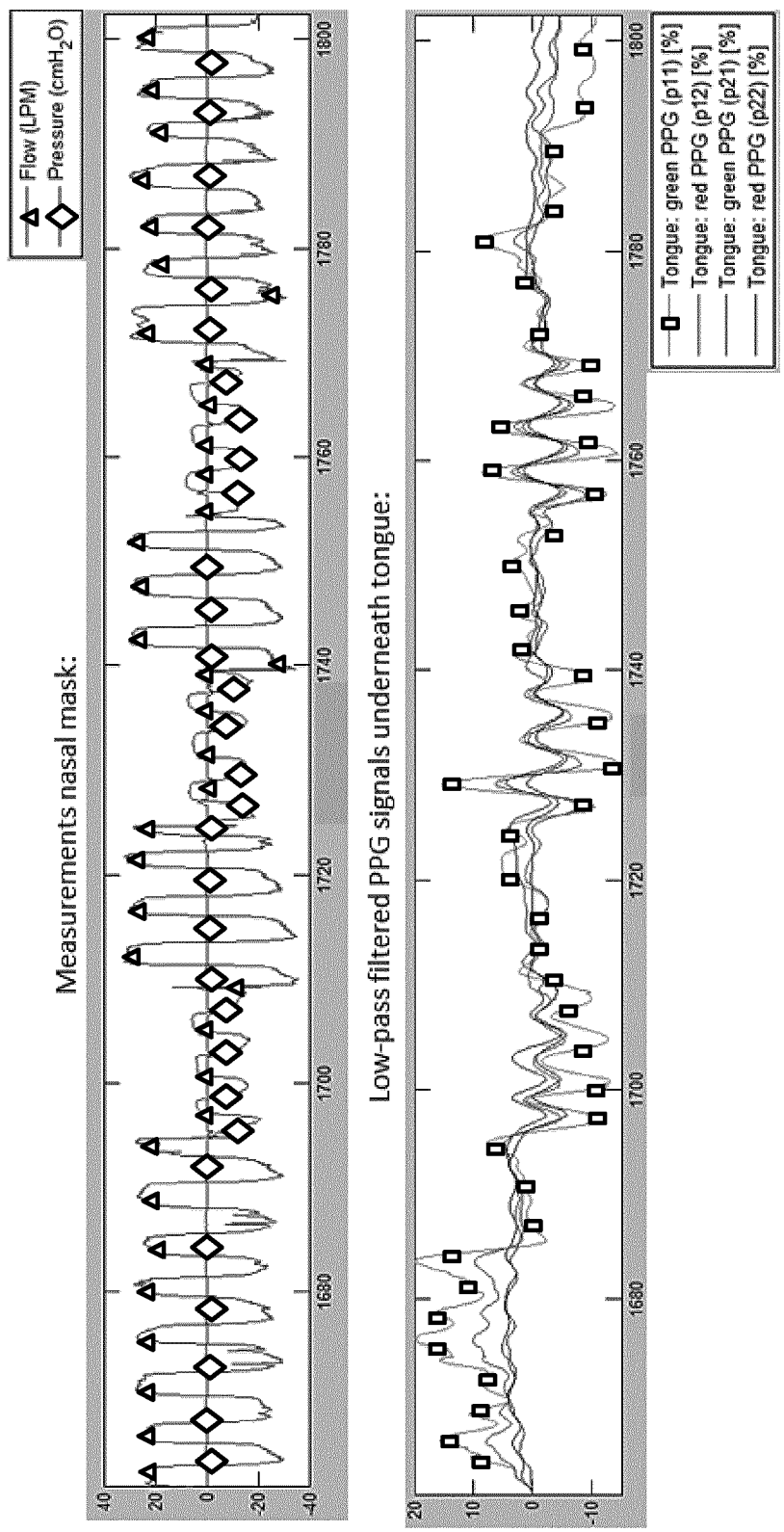
FIG. 5 depicts the results obtained by an experiment with the embodiment used for FIGS. 3 and 4, wherein obstructive sleep apnea (OSA) was mimicked by closing off the airflow to mouth and nose, while the patient was still trying to breath.

Turning now to FIG. 5, there is depicted the result of an experiment with the embodiment used for FIGS. 3 and 4, wherein obstructive sleep apnea (OSA) was mimicked by closing off the airflow to mouth and nose, while the patient was still trying to breath. The upper graph of FIG. 5 shows the flow and pressure measured with a nasal mask, while the lower graph shows the low-pass filtered PPG signals of the sublingual sensor. In episodes of obstruction, the flow and pressure measured by the mask are respectively constant and oscillating, while these episodes can be seen as large oscillations in the tongue sensor signals.

The obstruction leads to big pressure variations, which can be seen as large oscillations in the sublingual sensor signal. Central sleep apnea (CSA) does not show these large oscillations because, unlike OSA, CSA patients do not feature a significant respiration drive. In that way, it is possible to distinguish between OSA and CSA using the embodiment.

It is noted that, although a mask was used in the experiments that provided the results depicted in FIGS. 3, 4 and 5, the mask was used only for experimental purposes to measure the pressure in the upper airway, which corresponds to the intrathoracic pressure and the transmural pressure on the cardiac chambers and the blood vessels in the thorax when there is no airflow. In actual implementations, the sublingual sensor can be used as a stand-alone device.

By way of example of an implementation, in the presence of a General Practitioner (GP), a patient could be asked to wear the sensor and perform certain breathing manoeuvres, such as breathing very deep. The GP will then look at the sensor signal to come to a diagnosis.

Also, the sensor could be used during the night as relatively unobtrusive sensor for sleep analysis, without the need to wear an additional mask. Further, snoring can be seen in the PPG signal of the sublingual sensor as a high-frequency vibration (the high-frequency vibration of snoring is typically in the frequency range of 10 Hz to 1000 Hz. If the sublingual sensor unit also contains an accelerometer, the snoring could be seen as a high frequency component of the accelerometer signal as well. An embodiment of the sublingual sensor unit (with or without accelerometer) can therefore be used for snore detection. Embodiments may therefore be implemented as a sleep analysis tool.

In particular, as described above in the background section, HR, HRV, RR and RRV can be used together for sleep staging purposes, especially for discriminating REM, non- REM and awake periods. The proposed sublingual sensor arrangement is therefore suitable for sleep staging applications. Also, such sleep staging application may be made even more accurate by employing additional/supplementary sensors, such as an accelerometer adapted to measure patient activity, EMG electrodes to measure muscle tension of the tongue, and/or a pressure sensor to obtain a surrogate measurement for the tongue muscle tension.

Also, when at least two wavelengths are used to illuminate the tongue, the optical sensor in the sensor module can also measure blood oxygenation. Arterial blood oxygenation measured in this way (SpO2) is especially of interest in sleep analysis for people with sleep apnea.

In this way, features in the PPG and/or accelerometer signals can be used to identify events like yawning, apnea, teeth grinding, snoring, swallowing, etc. Also, as described above in relation to FIGS. 3, 4 and 5 OSA and CSA can even be discriminated with a sublingual sensor device according to an embodiment.

Each of yawning, teeth grinding, snoring, and swallowing disturb the PPG sensor signal in their own specific way, and this can be used for the purpose of recognizing such event. Further, the detection of the events can become even more specific when combined with an accelerometer signal from the same mouth piece or oral appliance. For example, motion features (in particular direction of motion with respect to the head, speed of motion and motion frequency) can be derived from the accelerometer signal and can be used to discriminate the different events.

It is noted, however, that a relation between the motion features and the events will likely depend on whether the sensor module is attached to the teeth with the tongue lying on top of it or attached to the tongue. In the first case, the sensor module will move when the lower jaw is moving (like in yawning and teeth grinding), while in the second case it will move together with the tongue (like in swallowing).

As an example of event detection, snoring will now be considered.

Snoring can be seen as a high-frequency component and increased amplitude in both the raw PPG and the accelerometer signal, as will now be illustrated with reference to FIG. 6.

Figure 6:
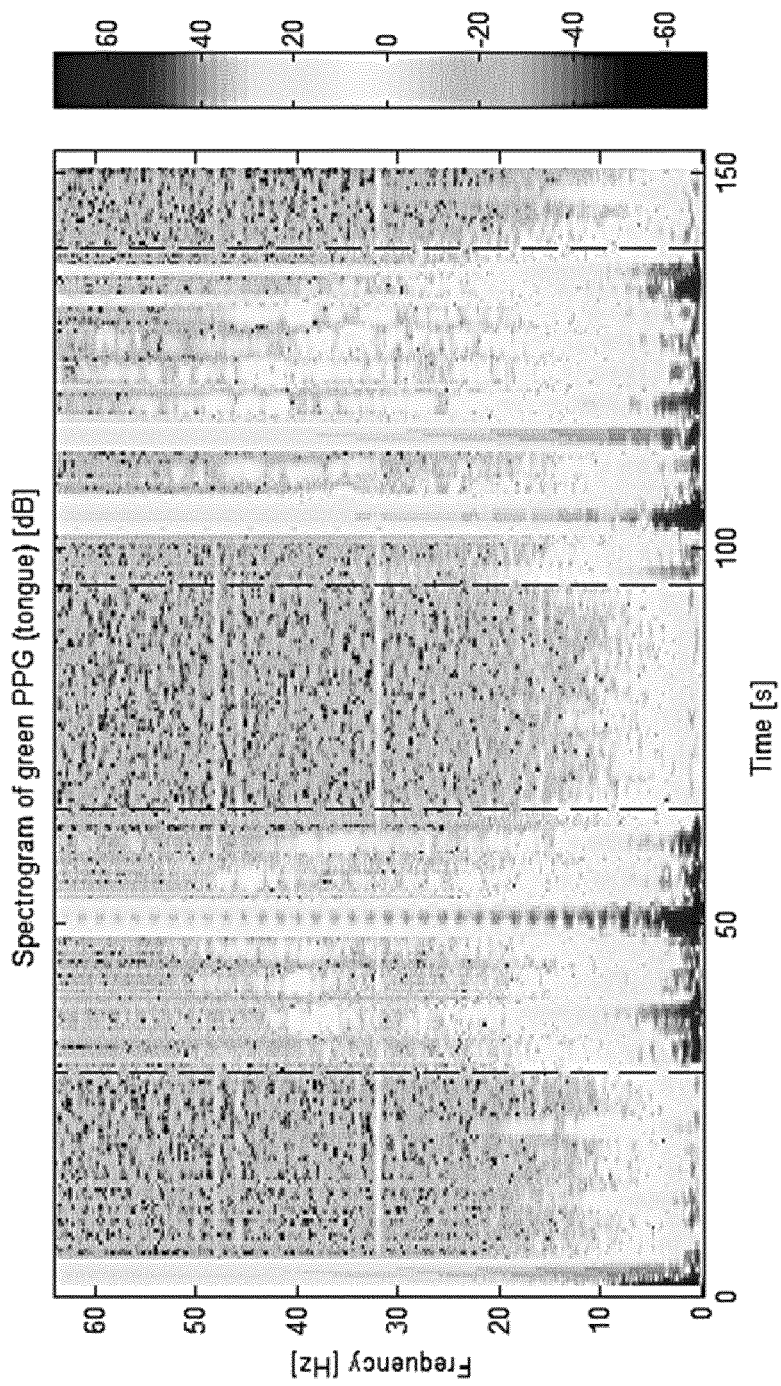
FIG. 6 is an exemplary spectrogram of a PPG signal obtained using a sublingual sensor device according to an embodiment.

FIG. 6 is an exemplary spectrogram of a PPG signal obtained using a sublingual sensor device according to an embodiment. Snoring periods (at 30-70 seconds and 95-140 seconds) can clearly be distinguished from non-snoring periods, because they show more power at higher frequencies. The snoring periods show bars separated in time because the snores were only taking place during inhalation and not during exhalation.

In this case, the snores only took place during inhalation and not during exhalation, resulting in pulsed power in high frequencies, visible as bars in FIG. 5. On top of that, the variation in heart rate (either derived from the heart rate data or from the heart rate variability data, which in turn are derived from the PPG signal) can be used to detect snoring. Frequency and/or amplitude analysis of the accelerometer and/or the PPG signal can therefore be used alone or in combination with HRV analysis to detect snoring.

In another embodiment, a microphone is added for additional or more specific analysis of sleep disordered breathing (in particular snoring and apnea).

Furthermore, sleep staging may be made more accurate when muscle tension is added as input next to HR, HRV, RR, RRV and activity. By way of example, electrodes might be added to the sublingual sensor module to measure EMG of the tongue. Alternatively, or additionally, a surrogate measurement for muscle tension might be obtained using a pressure sensor on the sensor module, wherein the pressure sensor is adapted to measure the pressure of the tongue on the sensor and thereby gives a measurement related to muscle tension/contact/activity.

The sensor signal might not be used solely as an input for deriving sleep stages, but might also be used to determine a signal quality of the optical sensor signal and/or its derived parameters. For example, when the contact between the tongue and the sensor module varies a lot, the optical signal will get a lot of artefacts and this might impact proper derivation of HR, HRV, RR and RRV. In a similar way, an accelerometer can be used to determine or infer the signal quality of the optical signal and/or its derived parameters. Further, a combination of the pressure signal and accelerometer signal might be used for this purpose.

Also, an accelerometer signal and/or pressure signal might be used to (at least partly) eliminate artefacts in the optical signal, thereby improving the reliability of the derived parameters.

Next to that, an accelerometer measures orientation with respect to the earth gravity field and can therefore be used to measure the orientation of the tongue/oral appliance and thereby the head orientation, which may be indicative for the patient's body posture.

Exemplary output parameters of a system according to an embodiment may therefore include information relating to one or more of the following:

sleep stages;
physiological signals, especially HR, HRV, RR, RRV and SpO2;
quality of the output, which gives the reliability of one or more parameters;
events: yawning, apnea (optionally divided in OSA and CSA), teeth grinding, snoring, swallowing, turning;
activity;
body posture;
relationship between posture and SDB (sleep disordered breathing) event (sleep apnea or snoring)/conclusion whether the patient has Positional OSA; and
relationship between posture and sleep stage;

Other parameters may be of less value to an end user (such as a medical professional or clinician) and might therefore not be provided as an output of the system, even though they may be used internally (for example to determine the sleep stages, for event detection, or for determining the quality of the output). This will likely be the case for signals like a raw PPG signal, motion features derived from the accelerometer and activity/contact/surrogate muscle tension measured by a pressure sensor.

Figure 7:
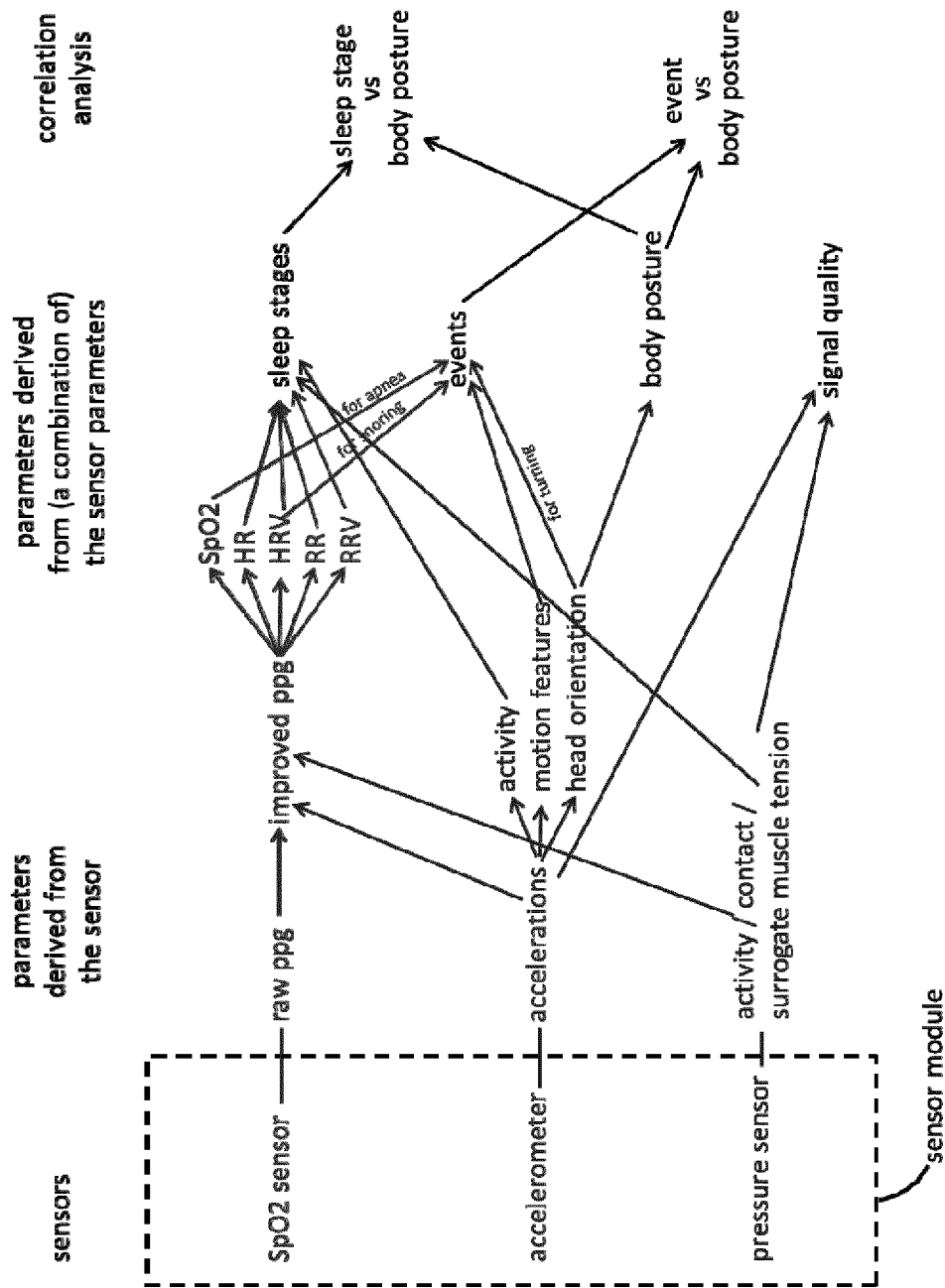
FIG. 7 is a diagram illustrating how various parameters may be derived from apparatus according to an embodiment comprising an SpO2 sensor as optical sensor, an accelerometer, and a pressure sensor.

Referring to FIG. 7, there is shown a diagram of a how various parameters may be derived from apparatus according to an embodiment comprising an SpO2 sensor as optical sensor, an accelerometer, and a pressure sensor.

In FIG. 7 arrows are used to indicate that the parameter at the start of the arrow might be used as input for determination of the parameter to which the arrow points.

Thus, by way of example, it can be seen from FIG. 6 that output signals from the accelerometer and pressure sensor can be used to obtain a refined (e.g. improved) PPG signal. Put another way, a cardio-respiratory value determined using a sublingual sensor output signal may be processed in combination with one or more supplementary sensor output signals to determine: a refined cardio-respiratory value; an indication of accuracy or reliability (e.g. signal quality); a sleep state/stage of the patient; an activity of the patient; or an indication of event occurrence.

Figure 8:
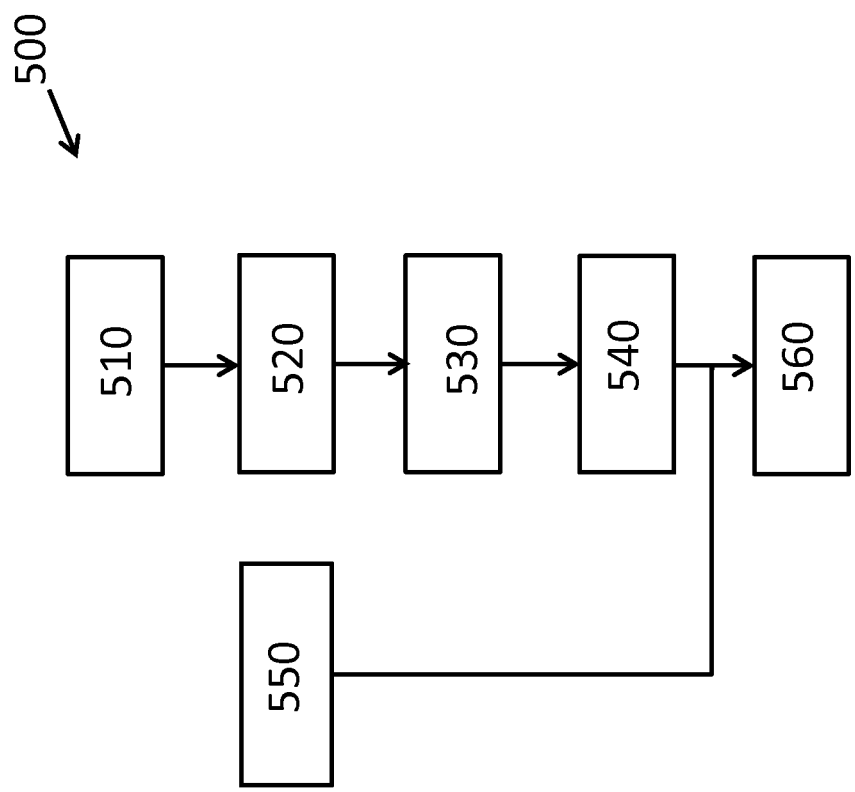
FIG. 8 is a flow diagram of a method for monitoring cardio-respiratory function of a patient according to an embodiment.

Turning now to FIG. 8, there is depicted a flow diagram of a method 500 for monitoring cardio-respiratory function of a patient according to an embodiment.

The method begins with step 510 of positioning a sublingual optical sensor unit at a sublingual vein of the patient's tongue. Here, the sublingual optical sensor unit is positioned under the patient's tongue towards the rear/back of the tongue and orientated so that the optical sensor of the sublingual optical sensor unit is facing and adjacent the sublingual vein of the tongue. Preferably, the optical sensor unit will be in contact with the underside of the tongue so that it is as close as practically possible to the sublingual vein.

Next, in step 520, the patient's tongue is illuminated with light from one or more light sources. Here, the step of illuminating the patient's tongue with light from a light source comprises positioning a light source against the tongue so that is adapted to shine light at the sublingual vein of the tongue. It also comprises controlling the one or more light sources to emit light having a wavelength within a first range of wavelengths and/or to emit light having a wavelength within a second, different range of wavelengths. More specifically, in this example, the first range of wavelengths comprises visible light and the second range of wavelengths comprises infra-red light. This may of course be different for other embodiments.

In step 530, light from the sublingual vein is detected by the sublingual optical sensor, and the sublingual optical sensor unit then generates a sensor output signal based on the detected light and communicates the sensor output signal to a processing unit in step 540.

Also, in step 550, a supplementary sensor output signal is generated by a supplementary sensor and communicated to the processing unit. More specifically, the supplementary sensor of this example comprises an accelerometer such that the supplementary sensor output signal comprises information relating to the patient's body posture and the sensed movement of the patient and of his tong and/or cheek.

Having received the sensor output signal and the supplementary sensor output signal, the processing unit then processed the received signals in step 560. Here, the processing unit processes the received signals in accordance with a data processing algorithm to determine both a cardio-respiratory value of the patient and at least one of: an indication of accuracy or reliability a sleep state of the patient; an activity and posture of the patient; and event detection and recognition.

More specifically, the sensor output signal is used to determine the cardio-respiratory value of the patient by identifying low-frequency variations in the sensor output signal. Also, the supplementary sensor output signal is used in combination with the determined cardio-respiratory value of the patient to determine at least one of an indication of accuracy or reliability a sleep state of the patient; an activity and posture of the patient; and event detection and recognition.

From the above description of the flow diagram in FIG. 8, it will be understood that embodiments may provide a concept for monitoring one or more cardio-respiratory functions of a patient. The proposed concept may comprise positioning an optical sensor at (e.g. adjacent, next to, neighbouring) a sublingual vein of the patient's tongue. Light transmitted through the sublingual vein may then be detected by the optical sensor and the detected light may be used (e.g. processed according to one or more algorithms) to determine a value of a cardio-respiratory functions of the patient. Determining the value of a cardio-respiratory function may comprise taking account of historical information relating to previously determined values of the cardio-respiratory function of the patient. Data can be stored (e.g. in an on-board memory storage unit or in a remotely provision database) for logging of values and events, or can be streamed (e.g. using an on-board antenna/transmitter), which would also enable alarm generation. Also a hybrid solution is possible, in which data are, by default, stored locally but, in the case of a particular event the antenna may be used to send an alarm.

Further, additional sensors may be employed to detect one or more supplementary values of other physical attributes or parameters of the patient. Such supplementary values may be used in combination with the detected light and/or determined value of the cardio-respiratory function to infer or determine other information (such as an indication of accuracy or reliability, a sleep state of the patient, an activity of the patient, or an indication of event occurrence for example) and/or confirm/validate the determined value of the cardio-respiratory function.

Thus, proposed concepts may be used to see the effect of treatment of SDB (sleep disordered breathing) or insomnia. In particular, when a mandibular advancement device (MAD) is used as treatment for SDB, the sensor module might be attached to the MAD. Embodiments might even be adapted to monitor restless leg syndrome or shaking of the head due to a neurological disorder and it might be used as arousal monitor, which can distinguish between a silent, motionless arousal and an arousal with gasping for air and/or turning the body.

Further, a temperature sensor (e.g. a thermistor) may be added to the sensor module to detect whether the patient's mouth is open or closed.

The sensor module may be (wirelessly) connected to an alarm clock, light, and/or the alarm clock on a mobile phone. The wake up moment can then be adapted to the sleep stages, e.g. avoid waking up the patient when he/she is in deep sleep. Also, a vibrator and/or speaker may be employed to wake up the patient when an event like sleep apnea or atrial fibrillation takes place.

Proposed embodiments might also facilitate early identification of Parkinson's disease, as sleep problems like insomnia, excessive daytime sleepiness, nightmares, sleep attacks (a sudden involuntary episode of sleep), and REM sleep behaviour disorder (acting out dreams during sleep) may be an early sign of Parkinson's disease, even before motor symptoms have begun.

For such purposes, proposed concepts may employ (or be employed on) at least one processor.

Thus, there may be provided a computer program product downloadable from a communications network and/or stored on a computer readable medium and/or microprocessor-executable medium wherein the computer program product comprises computer program code instructions, which when executed by at least one processor, implement a method according to a proposed embodiment.

Figure 9:
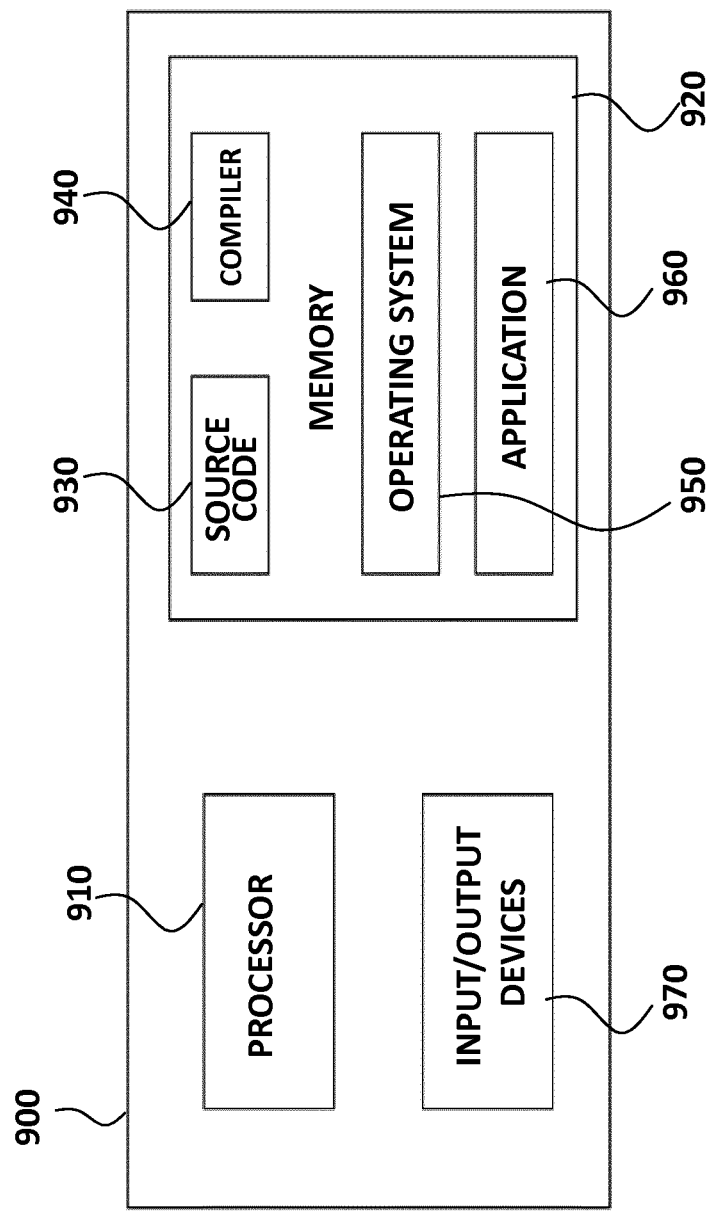
FIG. 9 illustrates an example of a computer within which one or more parts of an embodiment may be employed.

FIG. 9 illustrates an example of a computer 900 within which one or more parts of an embodiment may be employed. Various operations discussed above may utilize the capabilities of the computer 900. For example, one or more parts of an apparatus for monitoring cardio-respiratory function of a patient may be incorporated in any element, module, application, and/or component discussed herein.

The computer 900 includes, but is not limited to, PCs, workstations, laptops, PDAs, palm devices, servers, storages, and the like. Generally, in terms of hardware architecture, the computer 900 may include one or more processors 910, memory 920, and one or more I/O devices 970 (such as environmental sensors, infection source sensors, user susceptibility sensors, etc.) that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 910 is a hardware device for executing software that can be stored in the memory 920. The processor 910 can be virtually any custom made or commercially available processor, a central processing unit (CPU), a digital signal processor (DSP), or an auxiliary processor among several processors associated with the computer 900, and the processor 910 may be a semiconductor based microprocessor (in the form of a microchip) or a microprocessor.

The memory 920 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 920 may incorporate electronic, magnetic, optical, and/or other types of storage media. Note that the memory 920 can have a distributed architecture, where various components are situated remote from one another, but can be accessed by the processor 910.

The software in the memory 920 may include one or more separate programs, each of which comprises an ordered listing of executable instructions for implementing logical functions. The software in the memory 920 includes a suitable operating system (O/S) 950, compiler 940, source code 930, and one or more applications 960 in accordance with exemplary embodiments. As illustrated, the application 960 comprises numerous functional components for implementing the features and operations of the exemplary embodiments. The application 960 of the computer 900 may represent various applications, computational units, logic, functional units, processes, operations, virtual entities, and/or modules in accordance with exemplary embodiments, but the application 960 is not meant to be a limitation.

The operating system 950 controls the execution of other computer programs, and provides scheduling, input-output control, file and data management, memory management, and communication control and related services. It is contemplated by the inventors that the application 960 for implementing exemplary embodiments may be applicable on all commercially available operating systems.

Application 960 may be a source program, executable program (object code), script, or any other entity comprising a set of instructions to be performed. When a source program, then the program is usually translated via a compiler (such as the compiler 940), assembler, interpreter, or the like, which may or may not be included within the memory 920, so as to operate properly in connection with the O/S 950. Furthermore, the application 960 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, FORTRAN, COBOL, Perl, Java, ADA, .NET, and the like.

The I/O devices 970 may include input devices such as, for example but not limited to, a mouse, keyboard, scanner, microphone, camera, etc. Furthermore, the I/O devices 970 may also include output devices, for example but not limited to a printer, display, etc. Finally, the I/O devices 970 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 970 also include components for communicating over various networks, such as the Internet or intranet.

If the computer 900 is a PC, workstation, intelligent device or the like, the software in the memory 920 may further include a basic input output system (BIOS) (omitted for simplicity). The BIOS is a set of essential software routines that initialize and test hardware at start up, start the O/S 950, and support the transfer of data among the hardware devices. The BIOS is stored in some type of read-only-memory, such as ROM, PROM, EPROM, EEPROM or the like, so that the BIOS can be executed when the computer 900 is activated.

When the computer 900 is in operation, the processor 910 is configured to execute software stored within the memory 920, to communicate data to and from the memory 920, and to generally control operations of the computer 900 pursuant to the software. The application 960 and the O/S 950 are read, in whole or in part, by the processor 910, perhaps buffered within the processor 910, and then executed.

When the application 960 is implemented in software it should be noted that the application 960 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 960 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

Thus, there is proposed a concept for providing user guidance regarding cardio-respiratory function at a personal level which employs optical sensing of the sublingual vein of a person's tongue. By sensing variations in blood volume in the sublingual vein, information regarding cardio-respiratory interactions of the person may be obtained.

At this point, it is noted that the above described embodiments are merely example embodiments and that several extensions thereto and/or variations may be made. For example, several types of supplementary monitoring/sensing devices can be envisaged, including clip-on devices, smart textiles, mouth inserts, etc.

Data from the system may be combined with personal data on health and well-being to generate a personal profile of "safe" and "risky" activities, locations and interactions. Data may also be transmitted for the benefit of other peer users or patients interested in cardio-respiratory functions, and such data could serve as input to complication avoidance software.

Other suitable extensions and variations to the above disclosed embodiments will be apparent to the skilled person.

For example, embodiments may be adapted to implement flexible thresholds that can be adapted according to user and/or with respect to time. In this way, it may be possible to have more or less strict versions of algorithms used to create alerts or notifications.

Also, also mentioned above, the PPG sensor may comprise several light sources (e.g. LEDs) and/or several photo detectors. They may be arranged in an array-like structure. The optical sensor could also comprise a CCD chip or use laser-speckle technique.

In another embodiment, the PPG sensor may be a (remote) camera, for example a camera that a GP has in his hand. The patient may be asked to lift his/her tongue up (or have his/her tongue lifted up by an additional device) in order to make the area around the sublingual vein visible to the camera.

A preferred implementation may be to only inform a user when a cardio-respiratory issue or anomaly is detected. This may help to ensure a seamless solution without inhibiting social interaction.

The proposed concept has the advantage that a network of portable computing device with monitoring and/or communication functions can be easily transformed into a cardio-respiratory function monitoring system.

Aspects of the present invention may be embodied as a cardio-respiratory function monitoring method or system at least partially embodied by a portable computing device or distributed over separate entities including a portable computing device. Aspects of the present invention may take the form of a computer program product embodied in one or more computer-readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Such a system, apparatus or device may be accessible over any suitable network connection; for instance, the system, apparatus or device may be accessible over a network for retrieval of the computer readable program code over the network. Such a network may for instance be the Internet, a mobile communications network or the like. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fibre, a portable compact disc read-only memory (CD-ROM), an optical storage device, a magnetic storage device, or any suitable combination of the foregoing. In the context of the present application, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fibre cable, RF, etc., or any suitable combination of the foregoing.

Computer program code for carrying out the methods of the present invention by execution on the processor 110 may be written in any combination of one or more programming languages, including an object oriented programming language such as Java, Smalltalk, C++ or the like and conventional procedural programming languages, such as the "C" programming language or similar programming languages. The program code may execute entirely on the processor 110 as a stand-alone software package, e.g. an app, or may be executed partly on the processor 110 and partly on a remote server. In the latter scenario, the remote server may be connected to the head-mountable computing device 100 through any type of network, including a local area network (LAN) or a wide area network (WAN), or the connection may be made to an external computer, e.g. through the Internet using an Internet Service Provider.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions to be executed in whole or in part on the data processor 110 of the cardiopulmonary resuscitation coordination system including portable computing device, such that the instructions create means for implementing the functions/acts specified in the flowchart and/or block diagram block or blocks. These computer program instructions may also be stored in a computer-readable medium that can direct the cardiopulmonary resuscitation guidance system including the portable computing device to function in a particular manner.

The computer program instructions may, for example, be loaded onto the portable computing device 100 to cause a series of operational steps to be performed on the portable computing device 100 and/or the server 120, to produce a computer-implemented process such that the instructions which execute on the portable computing device 100 and/or the server 120 provide processes for implementing the functions/acts specified in the flowchart and/or block diagram block or blocks. The computer program product may form part of a patient monitoring system including a portable computing device.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. Apparatus for monitoring cardio-respiratory function of a patient, the apparatus comprising:
   a sublingual sensor unit adapted to be positioned at sublingual vasculature of the patient's tongue, to detect light from the sublingual vasculature and to generate a sensor output signal based on the detected light; and
   a processing unit adapted to receive the sensor unit output signal,
   wherein the processing unit is adapted to process the received sensor unit output in accordance with one or more data processing algorithms adapted to identify low-frequency variations in the sensor output signal to determine a cardio-respiratory value of the patient,
   wherein the one or more data processing algorithms are adapted to identify variations in a plurality of frequency ranges, the plurality of frequency ranges comprising at least two non-overlapping frequency ranges,
   wherein each frequency range in the plurality of frequency ranges corresponds to a unique type of cardio-respiratory value,
   wherein the cardio-respiratory value comprises a respiration rate,
   and wherein the data-processing algorithm is adapted to identify low-frequency variations in the range of 0.08-0.5 Hz.

2. The apparatus of claim 1, wherein the sensor unit is adapted to be aimed at the sublingual vasculature area on the bottom side of a patient's tongue, preferably in an area close to the base of the tongue.

3. The apparatus of claim 1, wherein the sensor unit is adapted to be positioned at, aimed at, or proximate the sublingual vein or sublingual venous vasculature of the patient's tongue, preferably at a distance less than 1 cm from the sublingual vein, and more preferably at a distance less than 3 mm from the sublingual vein.

4. The apparatus of claim 1, further comprising a supplementary sensor module adapted to be positioned in the patient's mouth and comprising a sensor arrangement adapted to sense a value of at least one of: movement; pressure; temperature; and sound and to generate a supplementary sensor output signal based on the sensed value(s).

5. The apparatus of claim 4, wherein the processing unit is adapted to receive the sensor output signal and the supplementary sensor output signal, to process the received sensor output signal in accordance with a data processing algorithm to determine a cardio-respiratory value of the patient, and to analyse the determined cardio-respiratory value in combination with the received supplementary sensor output signal to determine at least one of: a refined cardio-respiratory value; an indication of accuracy or reliability; a sleep state of the patient; an activity of the patient; the posture of the patient; and an indication of event occurrence.

6. The apparatus of claim 1, wherein the sublingual sensor unit comprises a photoplethysmography sensor.

7. The apparatus of claim 1, further comprising a light source adapted to illuminate the patient's tongue.

8. A mouthpiece comprising:
   a mouthpiece unit adapted to be positioned, in use, in the mouth of a patient; and
   apparatus for monitoring cardio-respiratory function of a patient according to claim 1.

9. The mouthpiece of claim 8, wherein the sublingual sensor unit is adapted to be movable with respect to the mouthpiece unit.

10. A method for monitoring cardio-respiratory function of a patient, the method comprising:
    positioning a sublingual sensor unit at sublingual vasculature of the patient's tongue;
    detecting light from the sublingual vasculature;
    generating a sensor output signal based on the detected light; and
    processing the received sensor unit output signal in accordance with one or more data processing algorithms adapted to identify low-frequency variations in the sensor output signal to determine a cardio-respiratory value of the patient,
    wherein the one or more data processing algorithms are adapted to identify variations in a plurality of frequency ranges, the plurality of frequency ranges comprising at least two non-overlapping frequency ranges,
    wherein each frequency range in the plurality of frequency ranges corresponds to a unique type of cardio-respiratory value,
    wherein the cardio-respiratory value comprises a respiration rate,
    and wherein processing the received signal in accordance with a data processing algorithm comprises identifying low-frequency variations in the range of 0.08-0.5 Hz.

11. The method of claim 10, further comprising:
    positioning a supplementary sensor module in the patient's mouth, the sensor module comprising a sensor arrangement adapted to sense a value of at least one of: movement; pressure; temperature; and sound;
    sensing, with the sensor arrangement, a value of at least one of: movement; pressure; temperature; and sound; and
    generating a supplementary sensor output signal based on the sensed value(s).

12. Computer program product downloadable from a communications network and/or stored on a computer readable medium and/or microprocessor-executable medium wherein the computer program product comprises computer program code instructions, which when executed by at least one processor, implement a method as claimed in claim 10.

* * * * *